(12) United States Patent
Borisevich et al.

(10) Patent No.: US 11,864,867 B2
(45) Date of Patent: Jan. 9, 2024

(54) CONTROL CIRCUIT FOR A LIGHT SOURCE IN AN OPTICAL MEASUREMENT SYSTEM BY APPLYING VOLTAGE WITH A FIRST POLARITY TO START AN EMISSION OF A LIGHT PULSE AND APPLYING VOLTAGE WITH A SECOND POLARITY TO STOP THE EMISSION OF THE LIGHT PULSE

(71) Applicant: HI LLC, Los Angeles, CA (US)

(72) Inventors: Alex Borisevich, Los Angeles, CA (US); Ryan Field, Culver City, CA (US)

(73) Assignee: HI LLC, Los Angeles, CA (US)

( * ) Notice: Subject to any disclaimer, the term of this patent is extended or adjusted under 35 U.S.C. 154(b) by 378 days.

(21) Appl. No.: 17/202,554

(22) Filed: Mar. 16, 2021

(65) Prior Publication Data

US 2021/0290067 A1    Sep. 23, 2021

Related U.S. Application Data

(60) Provisional application No. 63/038,485, filed on Jun. 12, 2020, provisional application No. 62/992,486, filed on Mar. 20, 2020.

(51) Int. Cl.
*G01J 1/44* (2006.01)
*A61B 5/00* (2006.01)
*H01S 5/062* (2006.01)

(52) U.S. Cl.
CPC .......... *A61B 5/0082* (2013.01); *A61B 5/4064* (2013.01); *A61B 5/6803* (2013.01);
(Continued)

(58) Field of Classification Search
CPC ..... A61B 5/00; A61B 5/40; A61B 5/68; G01J 1/44; H01S 5/04; H01S 5/06
(Continued)

(56) References Cited

U.S. PATENT DOCUMENTS

| 4,018,534 A | 4/1977 | Thorn et al. |
| 4,207,892 A | 6/1980 | Binder |

(Continued)

FOREIGN PATENT DOCUMENTS

| CN | 200950235 | 9/2007 |
| CN | 107865635 | 4/2018 |

(Continued)

OTHER PUBLICATIONS

International Search Report and Written Opinion received in International Application No. PCT/2020/027537, dated Sep. 7, 2020.
(Continued)

*Primary Examiner* — Que Tan Le
(74) *Attorney, Agent, or Firm* — ALG Intellectual Property, LLC

(57) ABSTRACT

An exemplary system includes a light source and a control circuit configured to apply voltage having a first polarity to the light source for a first time period to provide a threshold charge for the light source to start an emission of a light pulse that is directed at a target within a body. The control circuit is further configured to apply voltage having a second polarity opposite the first polarity to the light source for a second time period subsequent to the first time period to discharge the light source to stop the emission of the light pulse.

28 Claims, 19 Drawing Sheets

(52) U.S. Cl.
CPC ............... *G01J 1/44* (2013.01); *H01S 5/062* (2013.01); *A61B 2562/0238* (2013.01); *G01J 2001/442* (2013.01); *G01J 2001/4466* (2013.01)

(58) Field of Classification Search
USPC ............................................ 250/205, 214 R
See application file for complete search history.

(56) References Cited

U.S. PATENT DOCUMENTS

| | | | |
|---|---|---|---|
| 4,281,645 A | 8/1981 | Jobsis | |
| 4,321,930 A | 3/1982 | Jobsis | |
| 4,515,165 A | 5/1985 | Carroll | |
| 4,655,225 A | 4/1987 | Dahne et al. | |
| 4,928,248 A | 5/1990 | Takahashi et al. | |
| 4,963,727 A | 10/1990 | Cova | |
| 4,995,044 A | 2/1991 | Blazo | |
| 5,088,493 A | 2/1992 | Giannini | |
| 5,090,415 A | 2/1992 | Yamashita | |
| 5,309,458 A | 5/1994 | Carl | |
| 5,386,827 A | 2/1995 | Chance et al. | |
| 5,528,365 A | 6/1996 | Gonatas et al. | |
| 5,625,458 A | 4/1997 | Alfano et al. | |
| 5,761,230 A | 6/1998 | Pono et al. | |
| 5,853,370 A | 12/1998 | Chance et al. | |
| 5,895,984 A | 4/1999 | Renz | |
| 5,929,982 A | 7/1999 | Anderson | |
| 5,983,120 A | 11/1999 | Groner et al. | |
| 5,987,045 A | 11/1999 | Albares et al. | |
| 6,163,715 A | 12/2000 | Larsen et al. | |
| 6,240,309 B1 | 5/2001 | Yamashita et al. | |
| 6,384,663 B2 | 5/2002 | Cova et al. | |
| 6,541,752 B2 | 4/2003 | Zappa et al. | |
| 6,618,614 B1 | 9/2003 | Chance | |
| 6,640,133 B2 | 10/2003 | Yamashita | |
| 6,683,294 B1 | 1/2004 | Herbert et al. | |
| 6,748,254 B2 | 6/2004 | O'Neil | |
| 6,992,772 B2 | 1/2006 | Block | |
| 7,095,491 B2 | 8/2006 | Forstner et al. | |
| 7,356,365 B2 | 4/2008 | Schurman | |
| 7,507,596 B2 | 3/2009 | Yaung et al. | |
| 7,547,872 B2 | 6/2009 | Niclass et al. | |
| 7,613,504 B2 | 11/2009 | Rowe | |
| 7,667,400 B1 | 2/2010 | Goushcha | |
| 7,705,284 B2 | 4/2010 | Inoue et al. | |
| 7,714,292 B2 | 5/2010 | Agarwal et al. | |
| 7,774,047 B2 | 8/2010 | Yamashita et al. | |
| 7,899,506 B2 | 3/2011 | Xu et al. | |
| 8,026,471 B2 | 9/2011 | Itzler | |
| 8,078,250 B2 | 12/2011 | Chen et al. | |
| 8,082,015 B2 | 12/2011 | Yodh et al. | |
| 8,115,170 B2 | 2/2012 | Stellari et al. | |
| 8,168,934 B2 | 5/2012 | Niclass et al. | |
| 8,352,012 B2 | 1/2013 | Besio | |
| 8,633,431 B2 | 1/2014 | Kim | |
| 8,637,875 B2 | 1/2014 | Finkelstein et al. | |
| 8,754,378 B2 | 6/2014 | Prescher et al. | |
| 8,817,257 B2 | 8/2014 | Herve | |
| 8,937,509 B2 | 1/2015 | Xu et al. | |
| 8,986,207 B2 | 3/2015 | Li | |
| 9,012,860 B2 | 4/2015 | Nyman et al. | |
| 9,041,136 B2 | 5/2015 | Chia | |
| 9,058,081 B2 | 6/2015 | Baxter | |
| 9,076,707 B2 | 7/2015 | Harmon | |
| 9,101,279 B2 | 8/2015 | Ritchey et al. | |
| 9,131,861 B2 | 9/2015 | Ince et al. | |
| 9,157,858 B2 | 10/2015 | Claps | |
| 9,160,949 B2 | 10/2015 | Zhang et al. | |
| 9,176,241 B2 | 11/2015 | Frach | |
| 9,178,100 B2 | 11/2015 | Webster et al. | |
| 9,190,552 B2 | 11/2015 | Brunel et al. | |
| 9,201,138 B2 | 12/2015 | Eisele et al. | |
| 9,209,320 B1 | 12/2015 | Webster | |
| 9,257,523 B2 | 2/2016 | Schneider et al. | |
| 9,257,589 B2 | 2/2016 | Niclass et al. | |
| 9,299,732 B2 | 3/2016 | Webster et al. | |
| 9,299,873 B2 | 3/2016 | Mazzillo et al. | |
| 9,312,401 B2 | 4/2016 | Webster | |
| 9,316,735 B2 | 4/2016 | Baxter | |
| 9,331,116 B2 | 5/2016 | Webster | |
| 9,368,487 B1 | 6/2016 | Su et al. | |
| 9,401,448 B2 | 7/2016 | Bienfang et al. | |
| 9,407,796 B2 | 8/2016 | Dinten et al. | |
| 9,419,635 B2 | 8/2016 | Kumar et al. | |
| 9,431,439 B2 | 8/2016 | Soga et al. | |
| 9,442,201 B2 | 9/2016 | Schmand et al. | |
| 9,449,377 B2 | 9/2016 | Sarkar et al. | |
| 9,450,007 B1 | 9/2016 | Motta et al. | |
| 9,466,631 B2 | 10/2016 | Fallica et al. | |
| 9,476,979 B2 | 10/2016 | Drader et al. | |
| 9,478,579 B2 | 10/2016 | Dai et al. | |
| 9,529,079 B1 | 12/2016 | Droz | |
| 9,535,157 B2 | 1/2017 | Caley et al. | |
| 9,574,936 B2 | 2/2017 | Heinonen | |
| 9,625,580 B2 | 4/2017 | Kotelnikov et al. | |
| 9,627,569 B2 | 4/2017 | Harmon | |
| 9,634,826 B1 | 4/2017 | Park | |
| 9,639,063 B2 | 5/2017 | Dutton et al. | |
| 9,640,704 B2 | 5/2017 | Frey et al. | |
| 9,658,158 B2 | 5/2017 | Renna et al. | |
| 9,659,980 B2 | 5/2017 | McGarvey et al. | |
| 9,671,284 B1 | 6/2017 | Dandin | |
| 9,681,844 B2 | 6/2017 | Xu et al. | |
| 9,685,576 B2 | 6/2017 | Webster | |
| 9,702,758 B2 | 7/2017 | Nouri | |
| 9,728,659 B2 | 8/2017 | Hirigoyen et al. | |
| 9,741,879 B2 | 8/2017 | Frey et al. | |
| 9,753,351 B2 | 9/2017 | Eldada | |
| 9,767,246 B2 | 9/2017 | Dolinsky et al. | |
| 9,768,211 B2 | 9/2017 | Harmon | |
| 9,773,930 B2 | 9/2017 | Motta et al. | |
| 9,804,092 B2 | 10/2017 | Zeng et al. | |
| 9,812,438 B2 | 11/2017 | Schneider et al. | |
| 9,831,283 B2 | 11/2017 | Shepard et al. | |
| 9,851,302 B2 | 12/2017 | Mattioli Della Rocca et al. | |
| 9,867,250 B1 | 1/2018 | Powers et al. | |
| 9,869,753 B2 | 1/2018 | Eldada | |
| 9,881,963 B1 | 1/2018 | Chen et al. | |
| 9,882,003 B1 | 1/2018 | Aharoni | |
| 9,886,095 B2 | 2/2018 | Pothier | |
| 9,899,544 B1 | 2/2018 | Mazzillo et al. | |
| 9,899,557 B2 | 2/2018 | Muscara' et al. | |
| 9,939,316 B2 | 4/2018 | Scott et al. | |
| 9,939,536 B2 | 4/2018 | O'Neill et al. | |
| 9,946,344 B2 | 4/2018 | Ayaz et al. | |
| D817,553 S | 5/2018 | Aaskov et al. | |
| 9,983,670 B2 | 5/2018 | Coleman | |
| 9,997,551 B2 | 6/2018 | Mandai et al. | |
| 10,016,137 B1 | 7/2018 | Yang et al. | |
| D825,112 S | 8/2018 | Saez | |
| 10,056,415 B2 | 8/2018 | Na et al. | |
| 10,103,513 B1 | 10/2018 | Zhang et al. | |
| 10,141,458 B2 | 11/2018 | Zhang et al. | |
| 10,157,954 B2 | 12/2018 | Na et al. | |
| 10,158,038 B1 | 12/2018 | Do Valle et al. | |
| 10,219,700 B1 | 3/2019 | Yang et al. | |
| 10,256,264 B2 | 4/2019 | Na et al. | |
| 10,340,408 B1 | 7/2019 | Katnani | |
| 10,424,683 B1 | 9/2019 | Do Valle | |
| 10,483,125 B2 | 11/2019 | Inoue | |
| 10,515,993 B2 | 12/2019 | Field et al. | |
| 10,533,893 B2 | 1/2020 | Leonardo | |
| 10,558,171 B2 | 2/2020 | Kondo | |
| 10,594,306 B2 | 3/2020 | Dandin | |
| 10,627,460 B2 | 4/2020 | Alford et al. | |
| 10,697,829 B2 | 6/2020 | Delic | |
| 10,772,561 B2 | 9/2020 | Donaldson | |
| 10,809,796 B2 | 10/2020 | Armstrong-Muntner | |
| 10,825,847 B2 | 11/2020 | Furukawa | |
| 10,912,504 B2 | 2/2021 | Nakaji | |
| 10,976,386 B2 | 4/2021 | Alford | |
| 10,983,177 B2 | 4/2021 | Jiménez-Martínez | |
| 10,996,293 B2 | 5/2021 | Mohseni | |

(56) References Cited

U.S. PATENT DOCUMENTS

| | | |
|---|---|---|
| 11,006,876 B2 | 5/2021 | Johnson |
| 11,006,878 B2 | 5/2021 | Johnson |
| 2002/0195545 A1 | 12/2002 | Nishimura |
| 2004/0057478 A1 | 3/2004 | Saito |
| 2004/0078216 A1 | 4/2004 | Toto |
| 2004/0160996 A1 | 8/2004 | Giorgi et al. |
| 2005/0038344 A1 | 2/2005 | Chance |
| 2005/0061986 A1 | 3/2005 | Kardynal et al. |
| 2005/0124863 A1 | 6/2005 | Cook |
| 2005/0228291 A1 | 10/2005 | Chance |
| 2006/0171845 A1 | 8/2006 | Martin |
| 2006/0197452 A1 | 9/2006 | Zhang |
| 2007/0038116 A1 | 2/2007 | Yamanaka |
| 2007/0083097 A1 | 4/2007 | Fujiwara |
| 2008/0021341 A1 | 1/2008 | Harris et al. |
| 2009/0012402 A1 | 1/2009 | Mintz |
| 2009/0054789 A1 | 2/2009 | Kiguchi et al. |
| 2009/0163775 A1 | 6/2009 | Barrett |
| 2009/0313048 A1 | 12/2009 | Kahn et al. |
| 2010/0210952 A1 | 8/2010 | Taira et al. |
| 2010/0249557 A1 | 9/2010 | Besko et al. |
| 2010/0301194 A1 | 12/2010 | Patel |
| 2011/0208675 A1 | 8/2011 | Shoureshi et al. |
| 2011/0248175 A1 | 10/2011 | Frach |
| 2012/0016635 A1 | 1/2012 | Brodsky et al. |
| 2012/0029304 A1 | 2/2012 | Medina et al. |
| 2012/0083673 A1 | 4/2012 | Al-Ali et al. |
| 2012/0101838 A1 | 4/2012 | Lingard et al. |
| 2013/0015331 A1 | 1/2013 | Birk |
| 2013/0030267 A1 | 1/2013 | Lisogurski |
| 2013/0030270 A1 | 1/2013 | Chiou et al. |
| 2013/0032713 A1 | 2/2013 | Barbi et al. |
| 2013/0090541 A1 | 4/2013 | MacFarlane et al. |
| 2013/0144644 A1 | 6/2013 | Simpson |
| 2013/0221221 A1 | 8/2013 | Bouzid et al. |
| 2013/0225953 A1 | 8/2013 | Oliviero et al. |
| 2013/0342835 A1 | 12/2013 | Blacksberg |
| 2014/0027607 A1 | 1/2014 | Mordarski et al. |
| 2014/0028211 A1 | 1/2014 | Imam |
| 2014/0055181 A1 | 2/2014 | Chavpas |
| 2014/0066783 A1 | 3/2014 | Kiani |
| 2014/0171757 A1 | 6/2014 | Kawato et al. |
| 2014/0185643 A1 | 7/2014 | McComb et al. |
| 2014/0191115 A1 | 7/2014 | Webster et al. |
| 2014/0211194 A1 | 7/2014 | Pacala et al. |
| 2014/0217264 A1 | 8/2014 | Shepard |
| 2014/0275891 A1 | 9/2014 | Muehlemann et al. |
| 2014/0289001 A1 | 9/2014 | Shelton |
| 2014/0291481 A1 | 10/2014 | Zhang et al. |
| 2015/0038811 A1 | 2/2015 | Asaka |
| 2015/0038812 A1 | 2/2015 | Ayaz et al. |
| 2015/0041625 A1 | 2/2015 | Dutton |
| 2015/0041627 A1 | 2/2015 | Webster |
| 2015/0054111 A1 | 2/2015 | Niclass et al. |
| 2015/0057511 A1 | 2/2015 | Basu |
| 2015/0077279 A1 | 3/2015 | Song |
| 2015/0094552 A1 | 4/2015 | Golda |
| 2015/0150505 A1 | 6/2015 | Kaskoun et al. |
| 2015/0157262 A1 | 6/2015 | Schuessler |
| 2015/0157435 A1 | 6/2015 | Chasins et al. |
| 2015/0182136 A1 | 7/2015 | Durduran et al. |
| 2015/0192677 A1 | 7/2015 | Yu et al. |
| 2015/0200222 A1 | 7/2015 | Webster |
| 2015/0293224 A1 | 10/2015 | Eldada et al. |
| 2015/0327777 A1 | 11/2015 | Kostic et al. |
| 2015/0333095 A1 | 11/2015 | Fallica et al. |
| 2015/0364635 A1 | 12/2015 | Bodlovic et al. |
| 2016/0049765 A1 | 2/2016 | Eldada |
| 2016/0099371 A1 | 4/2016 | Webster |
| 2016/0119983 A1 | 4/2016 | Moore |
| 2016/0150963 A1 | 6/2016 | Roukes et al. |
| 2016/0161600 A1 | 6/2016 | Eldada et al. |
| 2016/0181302 A1 | 6/2016 | McGarvey et al. |
| 2016/0182902 A1 | 6/2016 | Guo |
| 2016/0218236 A1 | 7/2016 | Dhulla et al. |
| 2016/0247301 A1 | 8/2016 | Fang |
| 2016/0278715 A1 | 9/2016 | Yu et al. |
| 2016/0287107 A1 | 10/2016 | Szabados |
| 2016/0296168 A1 | 10/2016 | Abreu |
| 2016/0341656 A1 | 11/2016 | Liu et al. |
| 2016/0345880 A1 | 12/2016 | Nakaji et al. |
| 2016/0356718 A1 | 12/2016 | Yoon et al. |
| 2016/0357260 A1 | 12/2016 | Raynor et al. |
| 2017/0030769 A1 | 2/2017 | Clemens et al. |
| 2017/0047372 A1 | 2/2017 | McGarvey et al. |
| 2017/0052065 A1 | 2/2017 | Sharma et al. |
| 2017/0085547 A1 | 3/2017 | De Aguiar et al. |
| 2017/0118423 A1 | 4/2017 | Zhou et al. |
| 2017/0124713 A1 | 5/2017 | Jurgenson et al. |
| 2017/0131143 A1 | 5/2017 | Andreou et al. |
| 2017/0139041 A1 | 5/2017 | Drader et al. |
| 2017/0141100 A1 | 5/2017 | Tseng et al. |
| 2017/0164857 A1 | 6/2017 | Soulet De Brugiere |
| 2017/0176579 A1 | 6/2017 | Niclass et al. |
| 2017/0176596 A1 | 6/2017 | Shpunt et al. |
| 2017/0179173 A1 | 6/2017 | Mandai et al. |
| 2017/0186798 A1 | 6/2017 | Yang et al. |
| 2017/0202518 A1 | 7/2017 | Furman et al. |
| 2017/0265822 A1 | 9/2017 | Du |
| 2017/0276545 A1 | 9/2017 | Henriksson |
| 2017/0281086 A1 | 10/2017 | Donaldson |
| 2017/0299700 A1 | 10/2017 | Pacala et al. |
| 2017/0303789 A1 | 10/2017 | Tichauer et al. |
| 2017/0314989 A1 | 11/2017 | Mazzillo et al. |
| 2017/0363467 A1 | 12/2017 | Clemens et al. |
| 2017/0367650 A1 | 12/2017 | Wallois |
| 2018/0003821 A1 | 1/2018 | Imai |
| 2018/0014741 A1 | 1/2018 | Chou |
| 2018/0019268 A1 | 1/2018 | Zhang et al. |
| 2018/0020960 A1 | 1/2018 | Sarussi |
| 2018/0026147 A1 | 1/2018 | Zhang et al. |
| 2018/0027196 A1 | 1/2018 | Yang et al. |
| 2018/0033895 A1 | 2/2018 | Mazzillo et al. |
| 2018/0039053 A1 | 2/2018 | Kremer et al. |
| 2018/0045816 A1 | 2/2018 | Jarosinski et al. |
| 2018/0062345 A1 | 3/2018 | Bills et al. |
| 2018/0066986 A1 | 3/2018 | Kasai et al. |
| 2018/0069043 A1 | 3/2018 | Pan et al. |
| 2018/0070830 A1 | 3/2018 | Sutin et al. |
| 2018/0070831 A1 | 3/2018 | Sutin et al. |
| 2018/0081061 A1 | 3/2018 | Mandai et al. |
| 2018/0089531 A1 | 3/2018 | Geva et al. |
| 2018/0089848 A1 | 3/2018 | Yang et al. |
| 2018/0090526 A1 | 3/2018 | Mandai et al. |
| 2018/0090536 A1 | 3/2018 | Mandai et al. |
| 2018/0102442 A1 | 4/2018 | Wang et al. |
| 2018/0103528 A1 | 4/2018 | Moore |
| 2018/0103861 A1 | 4/2018 | Sutin et al. |
| 2018/0117331 A1 | 5/2018 | Kuzniecky |
| 2018/0120152 A1 | 5/2018 | Leonardo |
| 2018/0122560 A1 | 5/2018 | Okuda |
| 2018/0156660 A1 | 6/2018 | Turgeon |
| 2018/0167606 A1 | 6/2018 | Cazaux et al. |
| 2018/0175230 A1 | 6/2018 | Droz et al. |
| 2018/0180473 A1 | 6/2018 | Clemens et al. |
| 2018/0185667 A1 | 7/2018 | Huang |
| 2018/0217261 A1 | 8/2018 | Wang |
| 2018/0296094 A1 | 10/2018 | Nakamura |
| 2018/0366342 A1 | 12/2018 | Inoue et al. |
| 2019/0006399 A1 | 1/2019 | Otake et al. |
| 2019/0025406 A1* | 1/2019 | Krelboim ............... H01S 5/062 |
| 2019/0026419 A1 | 1/2019 | Demeyer |
| 2019/0088697 A1 | 3/2019 | Furukawa et al. |
| 2019/0091483 A1 | 3/2019 | Deckert |
| 2019/0113385 A1 | 4/2019 | Fukuchi |
| 2019/0120975 A1 | 4/2019 | Ouvrier-Buffet |
| 2019/0167211 A1 | 6/2019 | Everman et al. |
| 2019/0175068 A1 | 6/2019 | Everdell |
| 2019/0200888 A1 | 7/2019 | Poltorak |
| 2019/0209012 A1 | 7/2019 | Yoshimoto et al. |
| 2019/0261869 A1 | 8/2019 | Franceschini |
| 2019/0298158 A1 | 10/2019 | Dhaliwal |
| 2019/0343395 A1 | 11/2019 | Cussac |
| 2019/0355773 A1 | 11/2019 | Field et al. |

(56) References Cited

U.S. PATENT DOCUMENTS

| | | |
|---|---|---|
| 2019/0355861 A1 | 11/2019 | Katnani |
| 2019/0363210 A1 | 11/2019 | Do Valle |
| 2019/0378869 A1 | 12/2019 | Field et al. |
| 2019/0388018 A1 | 12/2019 | Horstmeyer |
| 2019/0391213 A1 | 12/2019 | Alford |
| 2020/0022581 A1 | 1/2020 | Vanegas |
| 2020/0041727 A1 | 2/2020 | Yamamoto |
| 2020/0044098 A1 | 2/2020 | Azuma |
| 2020/0056263 A1 | 2/2020 | Bhattacharyya |
| 2020/0057115 A1 | 2/2020 | Jiménez-Martínez |
| 2020/0057116 A1 | 2/2020 | Zorzos et al. |
| 2020/0060542 A1 | 2/2020 | Alford |
| 2020/0088811 A1 | 3/2020 | Mohseni |
| 2020/0109481 A1 | 4/2020 | Sobek |
| 2020/0123416 A1 | 4/2020 | Bhattacharyya |
| 2020/0136632 A1 | 4/2020 | Lin |
| 2020/0182692 A1 | 6/2020 | Lilic |
| 2020/0188030 A1 | 6/2020 | Kopper et al. |
| 2020/0191883 A1 | 6/2020 | Bhattacharyya |
| 2020/0196932 A1 | 6/2020 | Johnson et al. |
| 2020/0241094 A1 | 7/2020 | Alford |
| 2020/0253479 A1 | 8/2020 | Nurmikko |
| 2020/0256929 A1 | 8/2020 | Ledbetter et al. |
| 2020/0309873 A1 | 10/2020 | Ledbetter et al. |
| 2020/0315510 A1 | 10/2020 | Johnson |
| 2020/0334559 A1 | 10/2020 | Anderson |
| 2020/0337624 A1 | 10/2020 | Johnson |
| 2020/0341081 A1 | 10/2020 | Mohseni et al. |
| 2020/0348368 A1 | 11/2020 | Garber et al. |
| 2020/0381128 A1 | 12/2020 | Pratt |
| 2020/0390358 A1 | 12/2020 | Johnson |
| 2020/0393902 A1 | 12/2020 | Mann et al. |
| 2020/0400763 A1 | 12/2020 | Pratt |
| 2021/0015385 A1 | 1/2021 | Katnani |
| 2021/0011094 A1 | 2/2021 | Bednarke |
| 2021/0041512 A1 | 2/2021 | Pratt |
| 2021/0063510 A1 | 3/2021 | Ledbetter |
| 2021/0013974 A1 | 5/2021 | Seidman |
| 2021/0139742 A1 | 5/2021 | Seidman |
| 2021/0265512 A1 | 8/2021 | Ayel |
| 2021/0290064 A1 | 9/2021 | Do Valle |
| 2021/0294996 A1 | 9/2021 | Field |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| KR | 20170087639 A | 7/2017 |
| WO | 8804034 | 6/1988 |
| WO | 1999053577 | 10/1999 |
| WO | 2008144831 | 12/2008 |
| WO | 2011083563 | 7/2011 |
| WO | 2012135068 | 10/2012 |
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017083826 | 5/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |
| WO | 2019221784 | 11/2019 |

OTHER PUBLICATIONS

International Search Report and Written Opinion received in International Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/537,360, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.
Alayed, et al., "Characterization of a Time-Resolved Diffuse Optical Spectroscopy Prototype Using Low-Cost, Compact Single Photon Avalanche Detectors for Tissue Optics Applications," Sensors 2018, 18, 3680; doi:10.3390/s18113680, Oct. 29, 2018.
Bellis, et al., "Photon counting imaging: the DigitalAPD," Society of Photo-Optical Instrumentation Engineers (SPIE) Conference Series, Feb. 2006, vol. 6068, pp. 111-120.
Blutman, et al., "A 0.1 pJ Freeze Vernier Time-to-Digital Converter in 65nm CMOS," 2014 International Symposium on Circuits and Systems (ISCAS), Melbourne, Australia, Jun. 1-5, 2014.
Cambie, et al., "Every photon counts: understanding and optimizing photon paths in luminescent solar concentrator-based photomicroreactors (LSC-PMs)," React. Chem. Eng., 2017, 2, 561-566.
Contini, et al., "Photon migration through a turbid slab described by a model based on diffusion approximation. I. Theory," Appl. Opt. 36(19), 4587 (1997).
Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010.
Dalla Mora, et al., "Memory effect in silicon time-gated single-photon avalanche diodes," http://dx.doi.org/10.1063/1.4915332, Journal of Applied Physics 117, 114501, 2015.
De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487 Sep. 11-13, 2007.
Di Sieno, et al., "Probe-hosted large area silicon photomultiplier and high-throughput timing electronics for enhanced performance time-domain functional near-infrared spectroscopy," Biomed. Opt. Express 11(11), 6389 (2020).
Dutton, et al., "A Time-Correlated Single-Photon-Counting Sensor with 14GS/s Histogramming Time-to-Digital Converter," 2015 IEEE International Solid-State Circuits Conference ISSCC 2015 / SESSION 11 / Sensors and Imagers for Life Sciences / 11.5, Feb. 22-26, 2015.
Fishburn, et al., "Temporal Derivative Distribution Repair (TDDR): A motion correction method for fNIRS," Neuroimage. Jan. 1, 2019; 184: 171-179. doi:10.1016/j.neuroimage.2018.09.025.
Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.
Gallivanoni, et al., "Progress in Quenching Circuits for Single Photon Avalanche Diodes," IEEE Transactions on Nuclear Science, vol. 57, No. 6, Dec. 2010.

(56) References Cited

OTHER PUBLICATIONS

Gnecchi, et al.,"A 1x16 SiPM Array for Automotive 3D Imaging LIDAR Systems.", Proceedings of the 2017 International Image Sensor Workshop (IISW), Hiroshima, Japan, (2017).
Harmon, et al.,"Compound Semiconductor SPAD Arrays," LightSpin Technologies, http://www.lightspintech.com/publications.html (2013).
Henderson, et al., "A 192 × 128 Time Correlated SPAD Image Sensor in 40-nm CMOS Technology," IEEE Journal of Solid-State Circuits, 2019.
Henderson, et al.,"A 256×256 40nm/90nm CMOS 3D-Stacked 120dB Dynamic-Range Reconfigurable Time-Resolved SPAD Imager," 2019 IEEE International Solid- State Circuits Conference—(ISSCC), San Francisco, CA, USA, 2019, pp. 106-108. doi: 10.1109/ISSCC.2019.8662355.
Huikari, et al., "High-Energy Picosecond Pulse Generation by Gain Switching in Asymmetric Waveguide Structure Multiple Quantum Well Lasers," IEEE Journal of Selected Topics in Quantum Electronics, vol. 21, No. 6, Nov. / Dec. 2015.
Huppert, et al.,"HomER: a review of time-series analysis methods for near-infrared spectroscopy of the brain," Appl. Opt. 48(10), D280 (2009).
Kienle, et al.,"Improved solutions of the steady-state and the time-resolved diffusion equations for reflectance from a semi-infinite turbid medium," J. Opt. Soc. Am. A 14(1), 246 (1997).
Konugolu, et al., "Broadband (600-1350 nm) Time-Resolved Diffuse Optical Spectrometer for Clinical Use," IEEE Journal of Selected Topics in Quantum Electronics, vol. 22, No. 3, May/Jun. 2016.
Lacerenza, et al., "Wearable and wireless time-domain near-infrared spectroscopy system for brain and muscle hemodynamic monitoring," Biomed. Opt. Express 11(10), 5934 (2020).
Lange, et al.,"Clinical Brain Monitoring with Time Domain NIRS: A Review and Future Perspectives," Applied Sciences 9(8), 1612 (2019).
Lange, et al., "MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).
Lee, et al.,"High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).
Li, et al.,"Step-Puise Modulation of Gain-Switched Semiconductor Pulsed Laser," Appl. Sci. 2019, 9, 602; doi:10.3390/app9030602.
Mandai, et al., "A 4 X 4 X 416 digital SiPM array with 192 TDCs for multiple high-resolution timestamp acquisition," 2013 JINST 8 PO5024, May 31, 2013.
Martelli, et al.,"Optimal estimation reconstruction of the optical properties of a two-layered tissue phantom from time-resolved single-distance measurements," Journal of Biomedical Optics 20(11), 115001 (Nov. 2015).
Maruyama, et al.,"A 1024 × 8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014.
Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.
Mora, et al., "Fast silicon photomultiplier improves signal harvesting and reduces complexity in time-domain diffuse optics," Opt. Express 23(11), 13937 (2015).
Mora, et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.
Parmesan, et al.,"A 256 × 256 SPAD array with in-pixel Time to Amplitude Conversion for Fluorescence Lifetime Imaging Microscopy," Memory 900.M4, 2015.
Pifferi, et al., "Performance assessment of photon migration instruments: the MEDPHOT protocol," Applied Optics, 44(11), 2104-2114 (2005).
Prahl, et al., "Optical Absorption of Hemoglobin," http://omic.ogi.edu/spectra/hemoglobin/index.html (1999).
Puszka, et al.,"Time-resolved diffuse optical tomography using fast-gated single-photon avalanche diodes," Biomedical optics express, 2013, vol. 4, No. 8, pp. 1351-1365 (Year: 2013).
Re, et al.,"Multi-channel medical device for time domain functional near infrared spectroscopy based on wavelength space multiplexing," Biomed. Opt. Express 4(10), 2231 (2013).
Renna, et al.,"Eight-Wavelength, Dual Detection Channel Instrument for Near-Infrared Time-Resolved Diffuse Optical Spectroscopy," IEEE J. Select. Topics Quantum Electron. 25(1), 1-11 (2019).
Richardson, et al.,"A 32x32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A., pp. 77-80, CICC 2009, San Jose, U.S.A., Sep. 13, 2009. https://doi.org/doi:10.1109/CICC.2009.5280890.
Takai, et al.,"Single-Photon Avalanche Diode with Enhanced NIR-Sensitivity for Automotive LIDAR Systems," Sensors, 2016, 16(4): 459, pp. 1-9 (Year: 2016).
Torricelli, et al., "Time domain functional NIRS imaging for human brain mapping," NeuroImage 85, 28-50 (2014).
Wabnitz, et al., "Depth-selective data analysis for time-domain fNIRS: moments vs. time windows," Biomed. Opt. Express 11(8), 4224 (2020).
Wabnitz, et al., "Performance assessment of time-domain optical brain imagers, part 1: basic instrumental performance protocol," Journal of Biomedical Optics 19(8), 086010 (Aug. 2014).
Wabnitz, et al., "Performance assessment of time-domain optical brain imagers, part 2: nEUROPt protocol," Journal of Biomedical Optics 19(8), 086012 (Aug. 2014).
Wojtkiewicz, et al., "Self-calibrating time-resolved near infrared spectroscopy," Biomed. Opt. Express 10(5), 2657 (2019).
Zhang, et al.,"A CMOS SPAD Imager with Collision Detection and 128 Dynamically Reallocating TDCs for Single- Photon Counting and 3D Time-of-Flight Imaging," Sensors (Basel, Switzerland), 18(11), 4016. doi:10.3390/s18114016 Nov. 17, 2018.
Zucchelli, et al.,"Method for the discrimination of superficial and deep absorption variations by time domain fNIRS," 2013 OSA Dec. 1, 2013 | vol. 4. No. 12 | DOI:10.1364/BOE.4.002893 | Biomedical Optics Express 2893.
Chen, et al., "A PVT Insensitive Field Programmable Gate Array Time-to-digital Converter", 2013 IEEE Nordic-Mediterranean Workshop on Time-to-Digital Converters. Oct. 3, 2013.
Field, et al., "A 100-fps, Time-Correlated Single-PhotonCounting-Based Fluorescence-Lifetime Imager in 130-nm CMOS", IEEE Journal of Solid-State Circuits, vol. 49, No. 4, Apr. 2014.
Lebid, et al., "Multi-Timescale Measurements of Brain Responses in Visual Cortex During Functional Stimulation Using Time-Resolved Spectroscopy", SPIE vol. 5826. Dec. 31, 2005. p. 609, last paragraph—p. 610, paragraph 1.
Zheng, et al., "An Integrated Bias Voltage Control Method for SPAD Arrays", Oct. 1, 2018, IEEE Service Center.
"emojipedia.org", https://emojipedia.org (accessed May 27, 2021).
"International Search Report and Written Opinion received in International Application No. PCT/2021/018188".
"International Search Report and Written Opinion received in International Application No. PCT/US2021/018155".
"International Search Report and Written Opinion received in International Application No. PCT/US2021/018187".
"International Search Report and Written Opinion received in International Application No. PCT/US2021/018190".
"scienceofpeople.com/emojis", https://www.scienceofpeople.com/emojis/ (accessed May 27, 2021).
Hebert, et al.,"Spatiotemporal image correlation spectroscopy (STICS) theory, verification, and application to protein velocity mapping in living CHO cells", Biophysical journal 88, No. 5 (2005): 3601-3614.
Kheng, et al.,"Image Processing", https://www.comp.nus.edu.sg/~cs4243/lecture/imageproc.pdf, Mar. 9, 2014.

(56) References Cited

OTHER PUBLICATIONS

Sneha, et al.,"Understanding Correlation", https://www.allaboutcircuits.com/technical-articles/understanding-correlation/, Jan. 4, 2017.
Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.
Zucconi, et al.,"The Autocorrelation Function", https://www.alanzucconi.com/2016/06/06/autocorrelation-function/, Jun. 6, 2016.

\* cited by examiner

CONTROL CIRCUIT FOR A LIGHT SOURCE IN AN OPTICAL MEASUREMENT SYSTEM BY APPLYING VOLTAGE WITH A FIRST POLARITY TO START AN EMISSION OF A LIGHT PULSE AND APPLYING VOLTAGE WITH A SECOND POLARITY TO STOP THE EMISSION OF THE LIGHT PULSE

RELATED APPLICATIONS

The present application claims priority under 35 U.S.C. § 119(e) to U.S. Provisional Patent Application No. 62/992,486, filed on Mar. 20, 2020, and to U.S. Provisional Patent Application No. 63/038,485, filed on Jun. 12, 2020. These applications are incorporated herein by reference in their respective entireties.

BACKGROUND INFORMATION

Detecting neural activity in the brain (or any other turbid medium) is useful for medical diagnostics, imaging, neuroengineering, brain-computer interfacing, and a variety of other diagnostic and consumer-related applications. For example, it may be desirable to detect neural activity in the brain of a user to determine if a particular region of the brain has been impacted by reduced blood irrigation, a hemorrhage, or any other type of damage. As another example, it may be desirable to detect neural activity in the brain of a user and computationally decode the detected neural activity into commands that can be used to control various types of consumer electronics (e.g., by controlling a cursor on a computer screen, changing channels on a television, turning lights on, etc.).

Neural activity and other attributes of the brain may be determined or inferred by measuring responses of tissue within the brain to light pulses. Light pulses may be provided by light sources such as lasers that are controlled by control circuits of an optical measurement system.

A photodetector capable of detecting a single photon (i.e., a single particle of optical energy) is an example of a non-invasive detector that can be used in the optical measurement system to detect neural activity within the brain. An exemplary photodetector is implemented by a semiconductor-based single-photon avalanche diode (SPAD), which is capable of capturing individual photons with very high time-of-arrival resolution (a few tens of picoseconds).

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems, circuits, and methods controlling a light source (e.g., a laser diode) in an optical measurement system are described herein. For example, the systems, circuits, and methods described herein may be configured to control (e.g., drive) a laser diode to emit light pulses. The systems, circuits, and methods may control precise starting and stopping of the emission of the light pulses by controlling slew rates of current applied to the laser diode. The slew rates may be controlled by applying voltage having a first polarity to the laser diode and then applying voltage having a second polarity opposite the first polarity to the laser diode. In some examples, the voltage having the second polarity may be applied such that the current applied to the laser diode drops to a negative current, which may discharge the laser more rapidly than simply ceasing to apply the current. The slew rates may be further controlled by additional components of the control circuit, such as voltage levels provided by one or more voltage sources, inductors, capacitors, etc.

Such precise control of light pulse timing may provide light pulses that may enable accurate detection of neural activity. Additionally, calibrating the light pulses to a current profile or other characteristic of the laser diode may result in increased power efficiency. Further, elements and components of the circuits and systems described herein may provide for additional efficiencies in resources.

These and other advantages and benefits of the present systems, circuits, and methods are described more fully herein.

Figure 1:
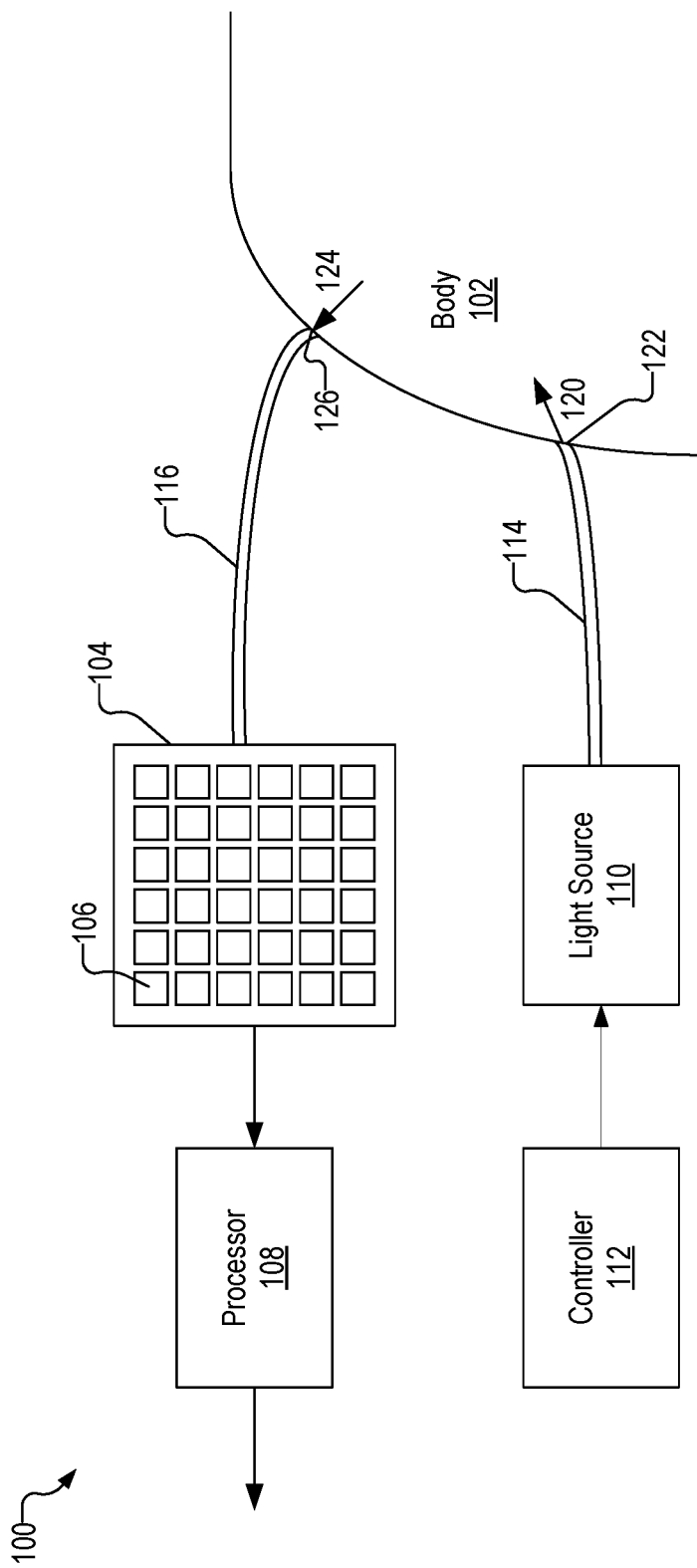
FIG. 1 shows an exemplary optical measurement system.

FIG. 1 shows an exemplary optical measurement system 100 configured to perform an optical measurement operation with respect to a body 102. Optical measurement system 100 may, in some examples, be portable and/or wearable by a user. Optical measurement systems that may be used in connection with the embodiments described herein are described more fully in U.S. patent application Ser. No. 17/176,315, filed Feb. 16, 2021; U.S. patent application Ser. No. 17/176,309, filed Feb. 16, 2021; U.S. patent application Ser. No. 17/176,460, filed Feb. 16, 2021; U.S. patent application Ser. No. 17/176,470, filed Feb. 16, 2021; U.S. patent application Ser. No. 17/176,487, filed Feb. 16, 2021; U.S. patent application Ser. No. 17/176,539, filed Feb. 16, 2021; U.S. patent application Ser. No. 17/176,560, filed Feb. 16, 2021; and U.S. patent application Ser. No. 17/176,466, filed Feb. 16, 2021, which applications are incorporated herein by reference in their entirety.

In some examples, optical measurement operations performed by optical measurement system 100 are associated with a time domain-based optical measurement technique. Example time domain-based optical measurement techniques include, but are not limited to, time-correlated single-photon counting (TCSPC), time domain near infrared spectroscopy (TD-NIRS), time domain diffusive correlation spectroscopy (TD-DCS), and time domain Digital Optical Tomography (TD-DOT). For example, TCSPC detects single photons and measures a time of arrival of the photons with respect to a reference signal (e.g., a light source). By repeating the light pulses, TCSPC may accumulate a sufficient number of photon events to statistically determine a histogram representing the distribution of detected photons. Based on the histogram of photon distribution, the response of tissue to light pulses may be determined in order to study the detected neural activity and/or other attributes of the brain.

As shown, optical measurement system 100 includes a detector 104 that includes a plurality of individual photodetectors (e.g., photodetector 106), a processor 108 coupled to detector 104, a light source 110, a controller 112, and optical conduits 114 and 116 (e.g., light pipes). However, one or more of these components may not, in certain embodiments, be considered to be a part of optical measurement system 100. For example, in implementations where optical measurement system 100 is wearable by a user, processor 108 and/or controller 112 may in some embodiments be separate from optical measurement system 100 and not configured to be worn by the user.

Detector 104 may include any number of photodetectors 106 as may serve a particular implementation, such as $2^n$ photodetectors (e.g., 256, 512, . . . , 16384, etc.), where n is an integer greater than or equal to one (e.g., 4, 5, 8, 10, 11, 14, etc.). Photodetectors 106 may be arranged in any suitable manner.

Photodetectors 106 may each be implemented by any suitable circuit configured to detect individual photons of light incident upon photodetectors 106. For example, each photodetector 106 may be implemented by a single photon avalanche diode (SPAD) circuit and/or other circuitry as may serve a particular implementation.

Processor 108 may be implemented by one or more physical processing (e.g., computing) devices. In some examples, processor 108 may execute instructions (e.g., software) configured to perform one or more of the operations described herein.

Light source 110 may be implemented by any suitable component configured to generate and emit light. For example, light source 110 may be implemented by one or more laser diodes. In some examples, the light emitted by light source 110 is high coherence light (e.g., light that has a coherence length of at least 5 centimeters) at a predetermined center wavelength.

Light source 110 is controlled by controller 112, which may be implemented by any suitable computing device (e.g., processor 108), integrated circuit, and/or combination of hardware and/or software as may serve a particular implementation. In some examples, controller 112 is configured to control light source 110 by turning light source 110 on and off and/or setting an intensity of light generated by light source 110. Controller 112 may be manually operated by a user, or may be programmed to control light source 110 automatically.

Light emitted by light source 110 may travel via an optical conduit 114 (e.g., a light pipe, a light guide, a waveguide, a single-mode optical fiber, and/or or a multi-mode optical fiber) to body 102 of a subject. In cases where optical conduit 114 is implemented by a light guide, the light guide may be spring loaded and/or have a cantilever mechanism to allow for conformably pressing the light guide firmly against body 102.

Body 102 may include any suitable turbid medium. For example, in some implementations, body 102 is a head or any other body part of a human or other animal. Alternatively, body 102 may be a non-living object. For illustrative purposes, it will be assumed in the examples provided herein that body 102 is a human head.

As indicated by arrow 120, the light emitted by light source 110 enters body 102 at a first location 122 on body 102. Accordingly, a distal end of optical conduit 114 may be positioned at (e.g., right above or physically attached to) first location 122 (e.g., to a scalp of the subject). In some examples, the light may emerge from optical conduit 114 and spread out to a certain spot size on body 102 to fall under a predetermined safety limit.

As used herein, "distal" means nearer, along the optical path of the light emitted by light source 110 or the light received by detector 104, to the target (e.g., within body 102) than to light source 110 or detector 104. Thus, the distal end of optical conduit 114 is nearer to body 102 than to light source 110, and the distal end of optical conduit 116 is nearer to body 102 than to detector 104. Additionally, as used herein, "proximal" means nearer, along the optical path of the light emitted by light source 110 or the light received by detector 104, to light source 110 or detector 104 than to body 102. Thus, the proximal end of optical conduit 114 is nearer to light source 110 than to body 102, and the proximal end of optical conduit 116 is nearer to detector 104 than to body 102.

As shown, the distal end of optical conduit 116 (e.g., a light pipe, a single-mode optical fiber, and/or or a multi-mode optical fiber) is positioned at (e.g., right above or physically attached to) output location 126 on body 102. In this manner, optical conduit 116 may collect light 124 as it exits body 102 at location 126 and carry the light to detector 104. The light may pass through one or more lenses and/or other optical elements (not shown) that direct the light onto each of the photodetectors 106 included in detector 104.

Photodetectors 106 may be connected in parallel in detector 104. An output of each of photodetectors 106 may be accumulated to generate an accumulated output of detector 104. Processor 108 may receive the accumulated output and determine, based on the accumulated output, a temporal distribution of photons detected by photodetectors 106. Processor 108 may then generate, based on the temporal distribution, a histogram representing a light pulse response of a target (e.g., brain tissue, blood flow, etc.) in body 102. Example embodiments of accumulated outputs are described herein.

Figure 2:
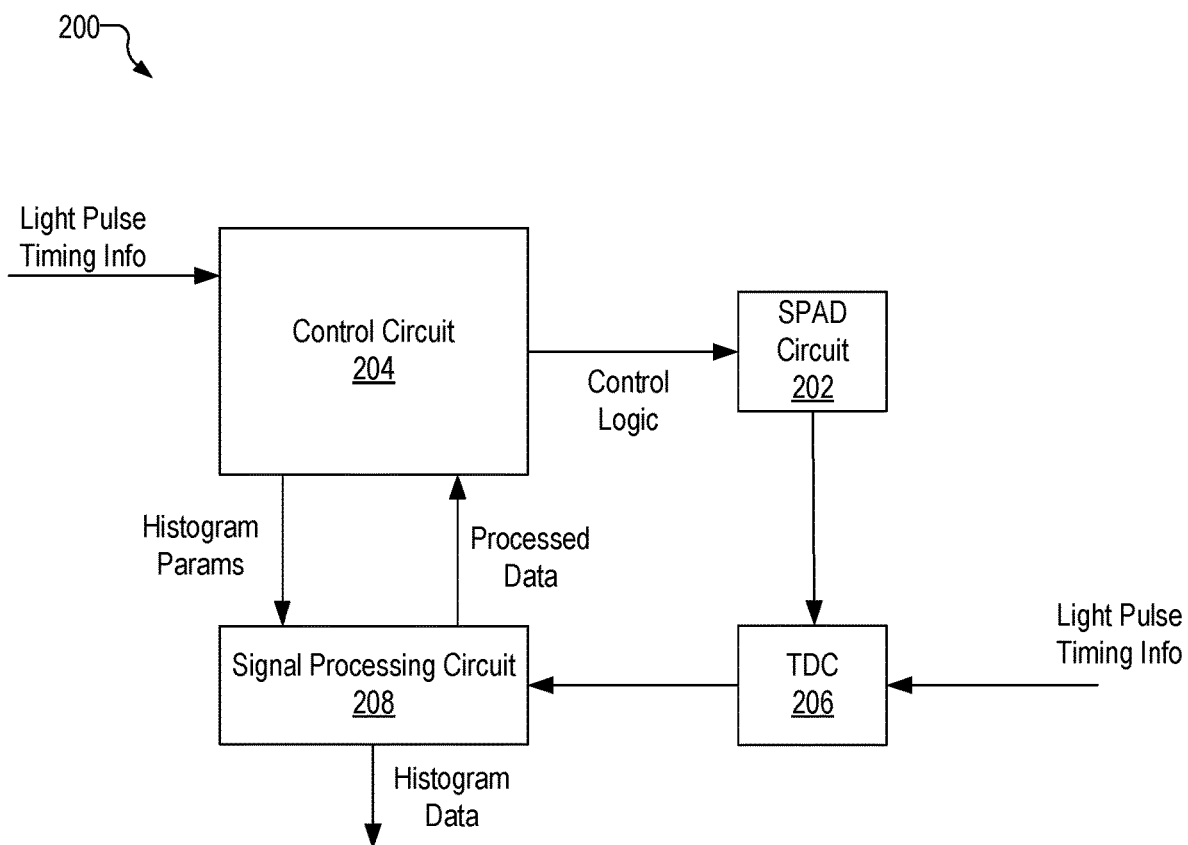
FIG. 2 illustrates an exemplary detector architecture.

FIG. 2 illustrates an exemplary detector architecture 200 that may be used in accordance with the systems and methods described herein. As shown, architecture 200 includes a SPAD circuit 202 that implements photodetector 106, a control circuit 204, a time-to-digital converter (TDC) 206, and a signal processing circuit 208. Architecture 200 may include additional or alternative components as may serve a particular implementation.

In some examples, SPAD circuit 202 includes a SPAD and a fast gating circuit configured to operate together to detect a photon incident upon the SPAD. As described herein, SPAD circuit 202 may generate an output when SPAD circuit 202 detects a photon.

The fast gating circuit included in SPAD circuit 202 may be implemented in any suitable manner. For example, the fast gating circuit may include a capacitor that is pre-charged with a bias voltage before a command is provided to arm the SPAD. Gating the SPAD with a capacitor instead of with an active voltage source, such as is done in some conventional SPAD architectures, has a number of advantages and benefits. For example, a SPAD that is gated with a capacitor may be armed practically instantaneously compared to a SPAD that is gated with an active voltage source. This is because the capacitor is already charged with the bias voltage when a command is provided to arm the SPAD. This is described more fully in U.S. Pat. Nos. 10,158,038 and 10,424,683, which are incorporated herein by reference in their entireties.

In some alternative configurations, SPAD circuit 202 does not include a fast gating circuit. In these configurations, the SPAD included in SPAD circuit 202 may be gated in any suitable manner or be configured to operate in a free running mode with passive quenching.

Control circuit 204 may be implemented by an application specific integrated circuit (ASIC) or any other suitable circuit configured to control an operation of various components within SPAD circuit 202. For example, control circuit 204 may output control logic that puts the SPAD included in SPAD circuit 202 in either an armed or a disarmed state.

In some examples, control circuit 204 may control a gate delay, which specifies a predetermined amount of time control circuit 204 is to wait after an occurrence of a light pulse (e.g., a laser pulse) to put the SPAD in the armed state. To this end, control circuit 204 may receive light pulse timing information, which indicates a time at which a light pulse occurs (e.g., a time at which the light pulse is applied to body 102). Control circuit 204 may also control a programmable gate width, which specifies how long the SPAD is kept in the armed state before being disarmed.

Control circuit 204 is further configured to control signal processing circuit 208. For example, control circuit 204 may provide histogram parameters (e.g., time bins, number of light pulses, type of histogram, etc.) to signal processing circuit 208. Signal processing circuit 208 may generate histogram data in accordance with the histogram parameters. In some examples, control circuit 204 is at least partially implemented by controller 112.

TDC 206 is configured to measure a time difference between an occurrence of an output pulse generated by SPAD circuit 202 and an occurrence of a light pulse. To this end, TDC 206 may also receive the same light pulse timing information that control circuit 204 receives. TDC 206 may be implemented by any suitable circuitry as may serve a particular implementation.

Signal processing circuit 208 is configured to perform one or more signal processing operations on data output by TDC 206. For example, signal processing circuit 208 may generate histogram data based on the data output by TDC 206 and in accordance with histogram parameters provided by control circuit 204. To illustrate, signal processing circuit 208 may generate, store, transmit, compress, analyze, decode, and/or otherwise process histograms based on the data output by TDC 206. In some examples, signal processing circuit 208 may provide processed data to control circuit 204, which may use the processed data in any suitable manner. In some examples, signal processing circuit 208 is at least partially implemented by processor 108.

In some examples, each photodetector 106 (e.g., SPAD circuit 202) may have a dedicated TDC 206 associated therewith. For example, for an array of N photodetectors 106, there may be a corresponding array of N TDCs 206. Alternatively, a single TDC 206 may be associated with multiple photodetectors 106. Likewise, a single control circuit 204 and a single signal processing circuit 208 may be provided for a one or more photodetectors 106 and/or TDCs 206.

Figure 3:
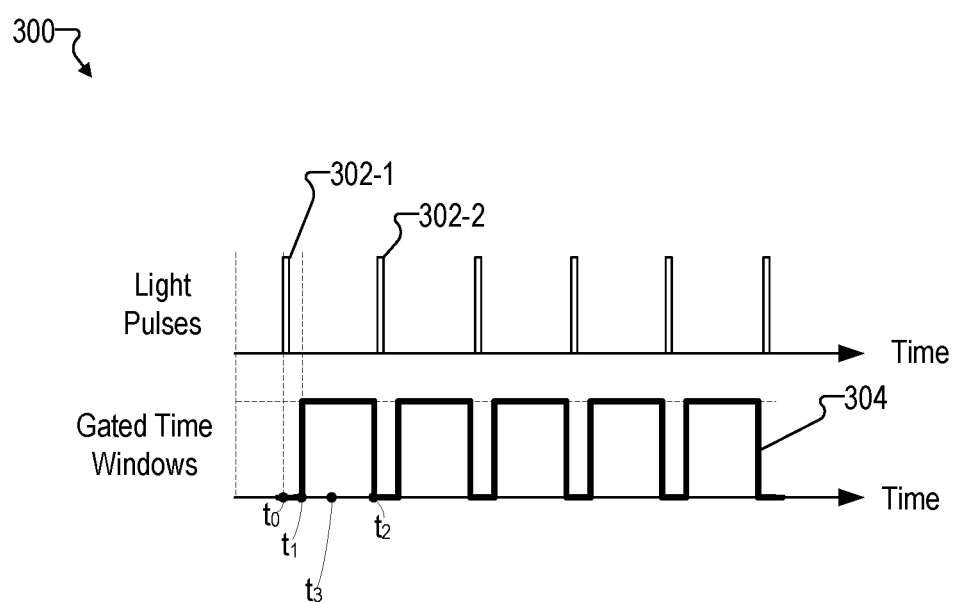
FIG. 3 illustrates an exemplary timing diagram for performing an optical measurement operation using an optical measurement system.

FIG. 3 illustrates an exemplary timing diagram 300 for performing an optical measurement operation using optical measurement system 100. Optical measurement system 100 may be configured to perform the optical measurement operation by directing light pulses (e.g., laser pulses) toward a target within a body (e.g., body 102). The light pulses may be short (e.g., 10-2000 picoseconds (ps)) and repeated at a high frequency (e.g., between 100,000 hertz (Hz) and 100 megahertz (MHz)). The light pulses may be scattered by the target and then detected by optical measurement system 100. Optical measurement system 100 may measure a time relative to the light pulse for each detected photon. By counting the number of photons detected at each time relative to each light pulse repeated over a plurality of light pulses, optical measurement system 100 may generate a histogram that represents a light pulse response of the target (e.g., a temporal point spread function (TPSF)). The terms histogram and TPSF are used interchangeably herein to refer to a light pulse response of a target.

For example, timing diagram 300 shows a sequence of light pulses 302 (e.g., light pulses 302-1 and 302-2) that may be applied to the target (e.g., tissue within a brain of a user, blood flow, a fluorescent material used as a probe in a body of a user, etc.). Timing diagram 300 also shows a pulse wave 304 representing predetermined gated time windows (also referred as gated time periods) during which photodetectors 106 are gated ON to detect photons. Referring to light pulse 302-1, light pulse 302-1 is applied at a time to. At a time $t_1$, a first instance of the predetermined gated time window begins. Photodetectors 106 may be armed at time $t_1$, enabling photodetectors 106 to detect photons scattered by the target during the predetermined gated time window. In this example, time $t_1$ is set to be at a certain time after time to, which may minimize photons detected directly from the laser pulse, before the laser pulse reaches the target. However, in some alternative examples, time $t_1$ is set to be equal to time to.

At a time $t_2$, the predetermined gated time window ends. In some examples, photodetectors 106 may be disarmed at time $t_2$. In other examples, photodetectors 106 may be reset (e.g., disarmed and re-armed) at time $t_2$ or at a time subsequent to time $t_2$. During the predetermined gated time window, photodetectors 106 may detect photons scattered by the target. Photodetectors 106 may be configured to remain armed during the predetermined gated time window such that photodetectors 106 maintain an output upon detecting a photon during the predetermined gated time window. For example, a photodetector 106 may detect a photon at a time $t_3$, which is during the predetermined gated time window between times $t_1$ and $t_2$. The photodetector 106 may be configured to provide an output indicating that the photodetector 106 has detected a photon. The photodetector 106 may be configured to continue providing the output until time $t_2$, when the photodetector may be disarmed and/or reset. Optical measurement system 100 may generate an accumulated output from the plurality of photodetectors. Optical measurement system 100 may sample the accumulated output to determine times at which photons are detected by photodetectors 106 to generate a TPSF.

As mentioned, in some alternative examples, photodetector 106 may be configured to operate in a free-running mode such that photodetector 106 is not actively armed and disarmed (e.g., at the end of each predetermined gated time window represented by pulse wave 304). In contrast, while operating in the free-running mode, photodetector 106 may be configured to reset within a configurable time period after an occurrence of a photon detection event (i.e., after photodetector 106 detects a photon) and immediately begin detecting new photons. However, only photons detected within a desired time window (e.g., during each gated time window represented by pulse wave 304) may be included in the TPSF.

Figure 4:
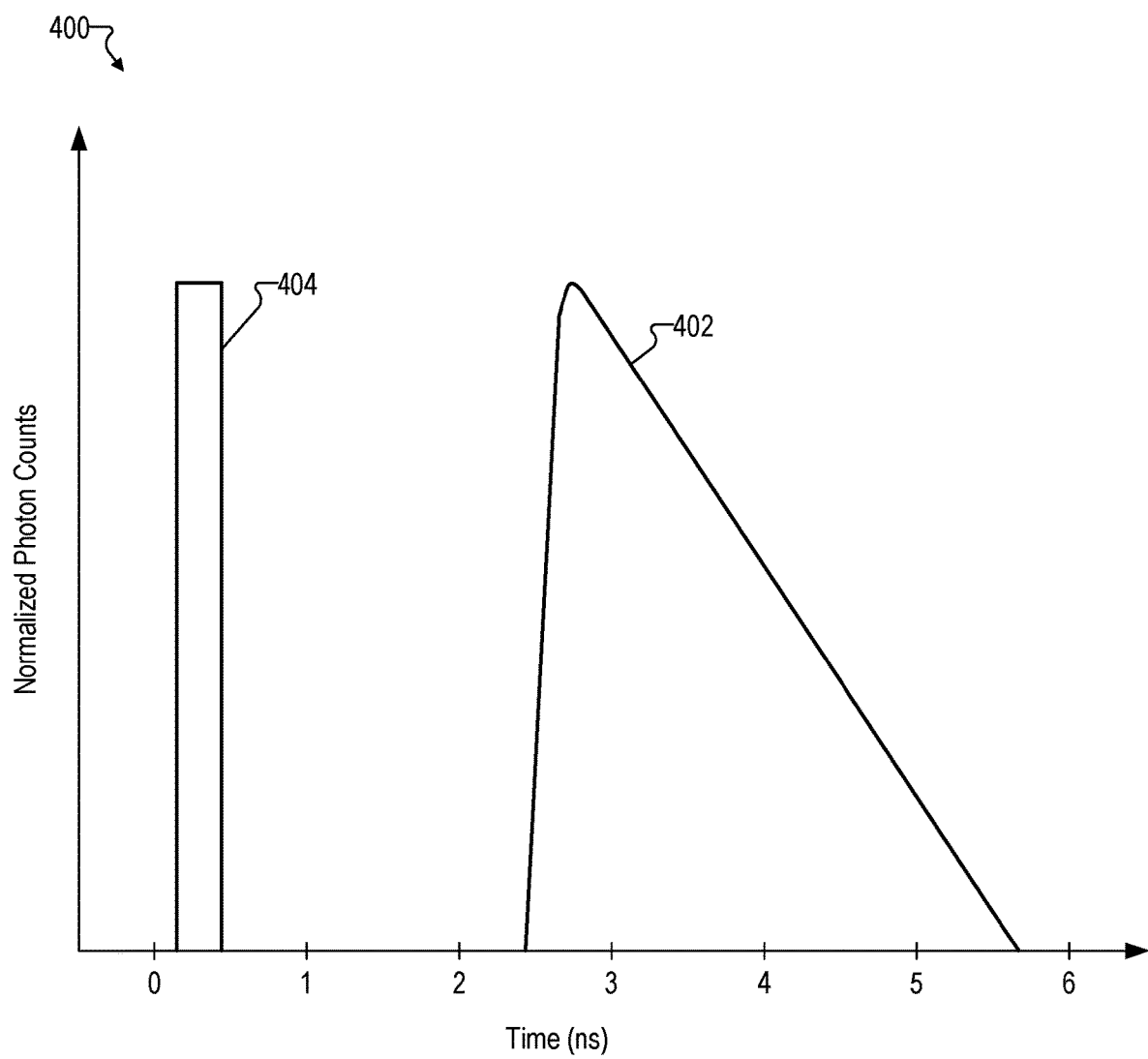
FIG. 4 illustrates a graph of an exemplary temporal point spread function that may be generated by an optical measurement system in response to a light pulse.

FIG. 4 illustrates a graph 400 of an exemplary TPSF 402 that may be generated by optical measurement system 100 in response to a light pulse 404 (which, in practice, represents a plurality of light pulses). Graph 400 shows a normalized count of photons on a y-axis and time bins on an x-axis. As shown, TPSF 402 is delayed with respect to a temporal occurrence of light pulse 404. In some examples, the number of photons detected in each time bin subsequent to each occurrence of light pulse 404 may be aggregated (e.g., integrated) to generate TPSF 402. TPSF 402 may be analyzed and/or processed in any suitable manner to determine or infer detected neural activity.

Optical measurement system 100 may be implemented by or included in any suitable device. For example, optical measurement system 100 may be included, in whole or in part, in a non-invasive wearable device (e.g., a headpiece) that a user may wear to perform one or more diagnostic, imaging, analytical, and/or consumer-related operations. The non-invasive wearable device may be placed on a user's head or other part of the user to detect neural activity. In some examples, such neural activity may be used to make behavioral and mental state analysis, awareness and predictions for the user.

Mental state described herein refers to the measured neural activity related to physiological brain states and/or mental brain states, e.g., joy, excitement, relaxation, surprise, fear, stress, anxiety, sadness, anger, disgust, contempt, contentment, calmness, focus, attention, approval, creativity, positive or negative reflections/attitude on experiences or the use of objects, etc. Further details on the methods and systems related to a predicted brain state, behavior, preferences, or attitude of the user, and the creation, training, and use of neuromes can be found in U.S. Provisional Patent Application No. 63/047,991, filed Jul. 3, 2020. Exemplary measurement systems and methods using biofeedback for awareness and modulation of mental state are described in more detail in U.S. patent application Ser. No. 16/364,338, filed Mar. 26, 2019, published as US2020/0196932A1. Exemplary measurement systems and methods used for detecting and modulating the mental state of a user using entertainment selections, e.g., music, film/video, are described in more detail in U.S. patent application Ser. No. 16/835,972, filed Mar. 31, 2020, published as US2020/0315510A1. Exemplary measurement systems and methods used for detecting and modulating the mental state of a user using product formulation from, e.g., beverages, food, selective food/drink ingredients, fragrances, and assessment based on product-elicited brain state measurements are described in more detail in U.S. patent application Ser. No. 16/853,614, filed Apr. 20, 2020, published as US2020/0337624A1. Exemplary measurement systems and methods used for detecting and modulating the mental state of a user through awareness of priming effects are described in more detail in U.S. patent application Ser. No. 16/885,596, filed May 28, 2020, published as US2020/0390358A1. These applications and corresponding U.S. publications are incorporated herein by reference in their entirety.

Figure 5:
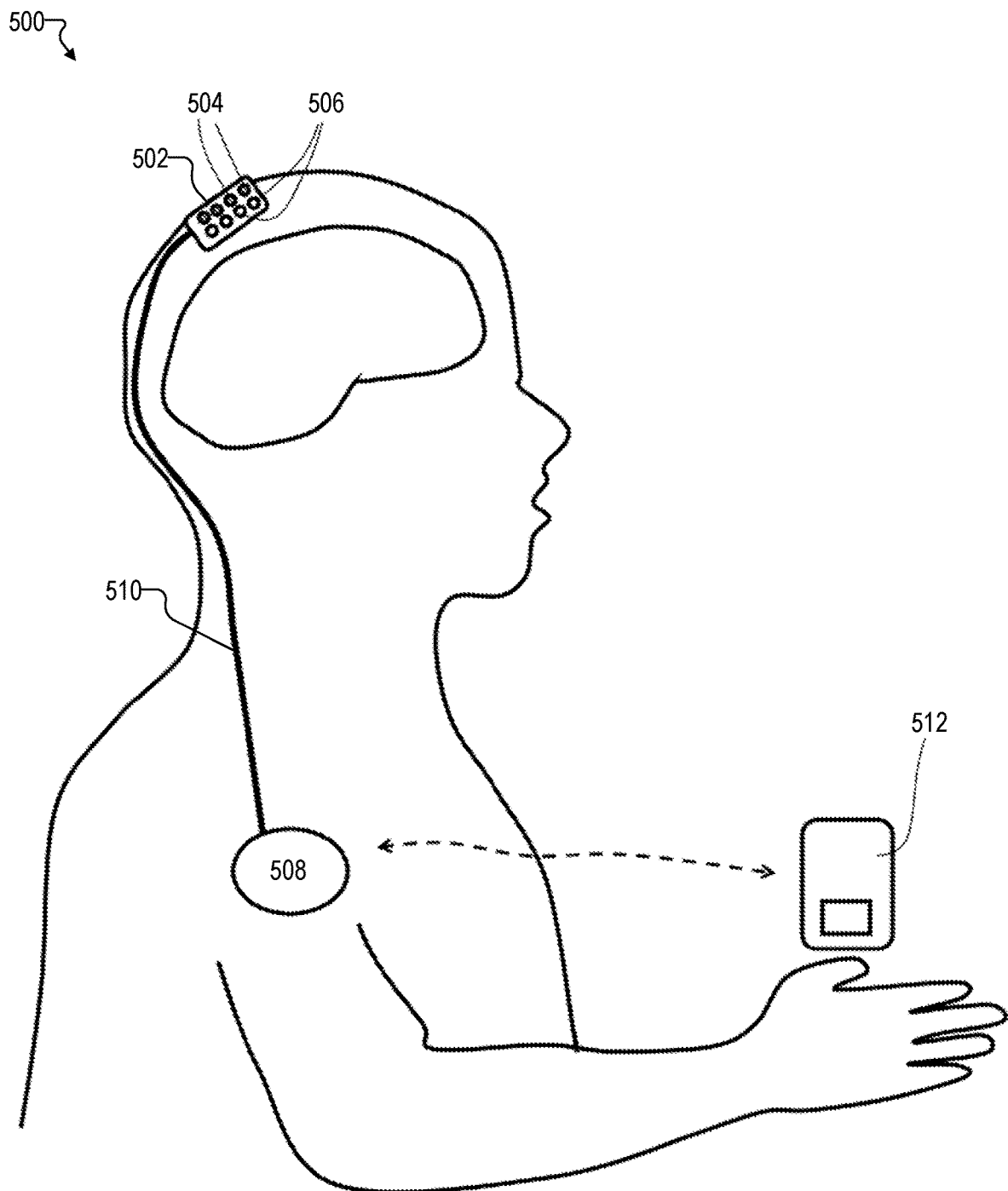
FIG. 5 shows an exemplary non-invasive wearable brain interface system.

FIG. 5 shows an exemplary non-invasive wearable brain interface system 500 ("brain interface system 500") that implements optical measurement system 100 (shown in FIG. 1). As shown, brain interface system 500 includes a head-mountable component 502 configured to be attached to a user's head. Head-mountable component 502 may be implemented by a cap shape that is worn on a head of a user. Alternative implementations of head-mountable component 502 include helmets, beanies, headbands, other hat shapes, or other forms conformable to be worn on a user's head, etc. Head-mountable component 502 may be made out of any suitable cloth, soft polymer, plastic, hard shell, and/or any other suitable material as may serve a particular implementation. Examples of headgears used with wearable brain interface systems are described more fully in U.S. Pat. No. 10,340,408, incorporated herein by reference in its entirety.

Head-mountable component 502 includes a plurality of detectors 504, which may implement or be similar to detector 104, and a plurality of light sources 506, which may be implemented by or be similar to light source 110. It will be recognized that in some alternative embodiments, head-mountable component 502 may include a single detector 504 and/or a single light source 506.

Brain interface system 500 may be used for controlling an optical path to the brain and for transforming photodetector measurements into an intensity value that represents an optical property of a target within the brain. Brain interface system 500 allows optical detection of deep anatomical locations beyond skin and bone (e.g., skull) by extracting data from photons originating from light source 506 and emitted to a target location within the user's brain, in contrast to conventional imaging systems and methods (e.g., optical coherence tomography (OCT)), which only image superficial tissue structures or through optically transparent structures.

Brain interface system 500 may further include a processor 508 configured to communicate with (e.g., control and/or receive signals from) detectors 504 and light sources 506 by way of a communication link 510. Communication link 510 may include any suitable wired and/or wireless communication link. Processor 508 may include any suitable housing and may be located on the user's scalp, neck, shoulders, chest, or arm, as may be desirable. In some variations, processor 508 may be integrated in the same assembly housing as detectors 504 and light sources 506.

As shown, brain interface system 500 may optionally include a remote processor 512 in communication with processor 508. For example, remote processor 512 may store measured data from detectors 504 and/or processor 508 from previous detection sessions and/or from multiple brain interface systems (not shown). Power for detectors 504, light sources 506, and/or processor 508 may be provided via a wearable battery (not shown). In some examples, processor 508 and the battery may be enclosed in a single housing, and wires carrying power signals from processor 508 and the battery may extend to detectors 504 and light sources 506. Alternatively, power may be provided wirelessly (e.g., by induction).

In some alternative embodiments, head mountable component 502 does not include individual light sources. Instead, a light source configured to generate the light that is detected by detector 504 may be included elsewhere in brain interface system 500. For example, a light source may be included in processor 508 and coupled to head mountable component 502 through optical connections.

Each of the light sources described herein may be implemented by any suitable device. For example, a light source as used herein may be, for example, a distributed feedback (DFB) laser, a super luminescent diode (SLD), a light emitting diode (LED), a diode-pumped solid-state (DPSS) laser, a laser diode (LD), a super luminescent light emitting diode (sLED), a vertical-cavity surface-emitting laser (VC- SEL), a titanium sapphire laser, a micro light emitting diode (mLED), and/or any other suitable laser or light source.

Optical measurement system 100 may alternatively be included in a non-wearable device (e.g., a medical device and/or consumer device that is placed near the head or other body part of a user to perform one or more diagnostic, imaging, and/or consumer-related operations). Optical measurement system 100 may alternatively be included in a sub-assembly enclosure of a wearable invasive device (e.g., an implantable medical device for brain recording and imaging).

Optical measurement system 100 may be modular in that one or more components of optical measurement system 100 may be removed, changed out, or otherwise modified as may serve a particular implementation. Additionally or alternatively, optical measurement system 100 may be modular such that one or more components of optical measurement system 100 may be housed in a separate housing (e.g., module) and/or may be movable relative to other components. Exemplary modular multimodal measurement systems are described in more detail in U.S. patent application Ser. No. 17/176,460, filed Feb. 16, 2021, U.S. patent application Ser. No. 17/176,470, filed Feb. 16, 2021, U.S. patent application Ser. No. 17/176,487, filed Feb. 16, 2021, U.S. Provisional Patent Application No. 63/038,481, filed Jun. 12, 2020, and U.S. patent application Ser. No. 17/176,560, filed Feb. 16, 2021, which applications are incorporated herein by reference in their respective entireties.

Figure 6:
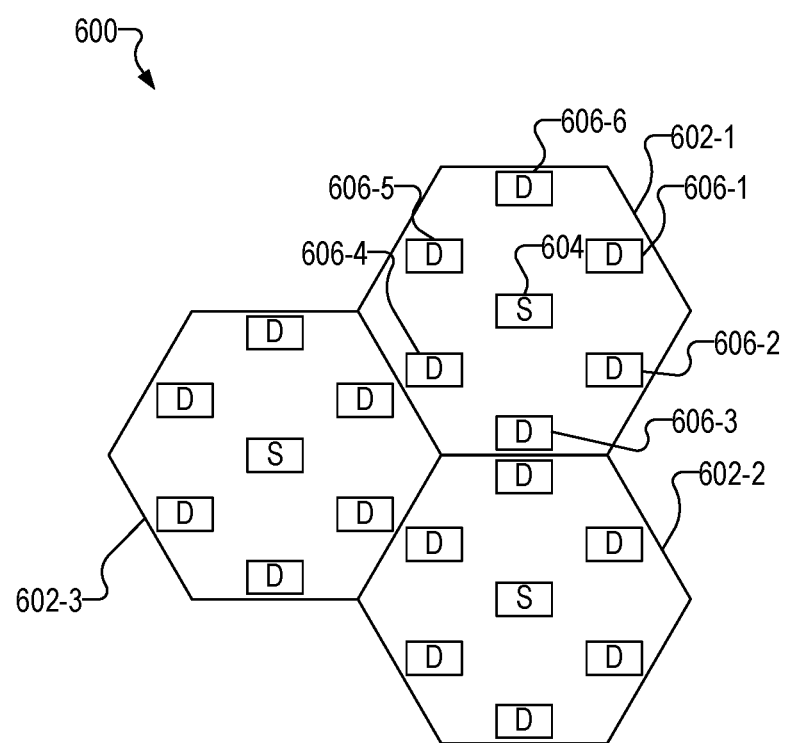
FIG. 6 shows an exemplary wearable module assembly.

To illustrate, FIG. 6 shows an exemplary wearable module assembly 600 ("assembly 600") that implements one or more of the optical measurement features described herein. Assembly 600 may be worn on the head or any other suitable body part of the user. As shown, assembly 600 may include a plurality of modules 602 (e.g., modules 602-1 through 602-3). While three modules 602 are shown to be included in assembly 600 in FIG. 6, in alternative configurations, any number of modules 602 (e.g., a single module up to sixteen or more modules) may be included in assembly 600. Moreover, while modules 602 are shown to be adjacent to and touching one another, modules 602 may alternatively be spaced apart from one another (e.g., in implementations where modules 602 are configured to be inserted into individual slots or cutouts of the headgear).

The wearable module assembly 600 may also conform to three-dimensional surface geometries, such as a user's head. Exemplary wearable module assemblies comprising a plurality of wearable modules are described in more detail in U.S. Provisional Patent Application No. 62/992,550, filed Mar. 20, 2020, which application is incorporated herein by reference in its entirety.

Each module 602 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors (e.g., SPADs) as well as other circuitry (e.g., TDCs). As shown, detectors 606 are arranged around and substantially equidistant from source 604. In other words, the spacing between a light source (i.e., a distal end portion of a light source optical conduit) and the detectors (i.e., distal end portions of optical conduits for each detector) are maintained at the same fixed distance on each module to ensure homogeneous coverage over specific areas and to facilitate processing of the detected signals. The fixed spacing also provides consistent spatial (lateral and depth) resolution across the target area of interest, e.g., brain tissue. Moreover, maintaining a known distance between the light emitter and the detector allows subsequent processing of the detected signals to infer spatial (e.g., depth localization, inverse modeling) information about the detected signals. Detectors 606 may be alternatively disposed as may serve a particular implementation.

Figure 7:
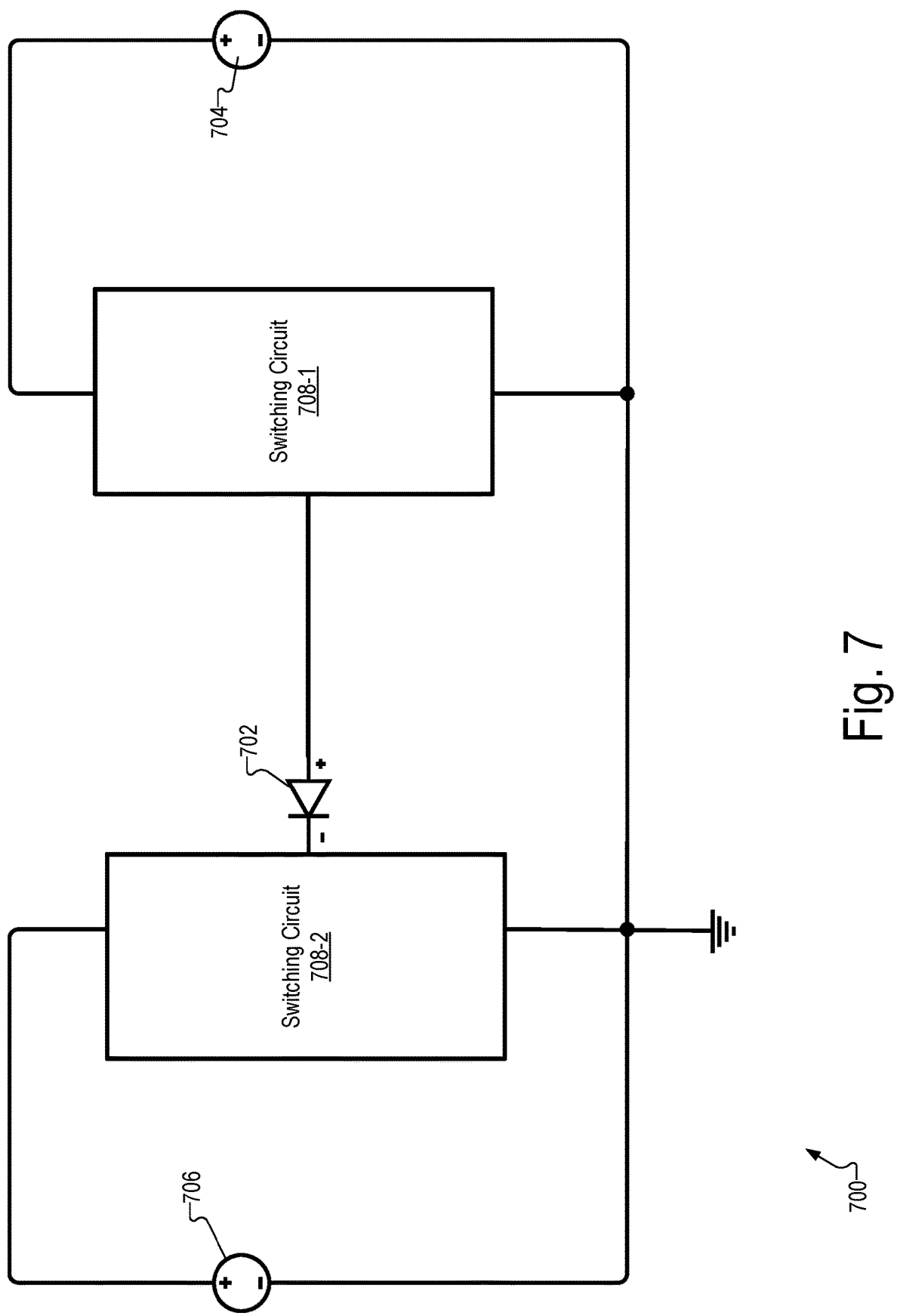
FIGS. 7-8 show exemplary control circuits for a laser diode.

FIG. 7 shows an exemplary control circuit 700 coupled to a laser diode 702. Laser diode 702 may be an implementation of light source 110 of optical measurement system 100 (shown in FIG. 1). Control circuit 700 may be implemented by controller 112 or a portion of controller 112 (shown in FIG. 1). While the light source in FIG. 7 is shown as a laser diode, the light source may be any suitable light source that may be controlled by control circuits as described herein.

Control circuit 700 includes a charging voltage source 704, a discharging voltage source 706, and a switching circuit 708 (e.g., switching circuit 708-1 and 708-2). Control circuit 700 may include additional or alternative components as may serve a particular implementation.

Charging voltage source 704 and discharging voltage source 706 may be implemented by any suitable component and/or circuit that provides a voltage. Switching circuit 708 may be configured to selectively couple charging voltage source 704 and discharging voltage source 706 to laser diode 702 to charge and discharge laser diode 702.

Laser diode 702 may be configured to emit light once a current applied to laser diode 702 meets a threshold current and supplies a threshold charge to laser diode 702. While the current applied to laser diode 702 supplies at least the threshold charge, laser diode 702 may be configured to continue to emit light. Once the current applied to laser diode 702 is reduced and laser diode 702 is discharged to below the threshold charge, laser diode 702 may stop emitting light. Thus, by controlling the current applied to laser diode 702, control circuit 700 may cause laser diode 702 to emit a light pulse.

Control circuit 700 may be configured to control the current applied to laser diode 702 by applying a voltage having a first polarity to laser diode 702 to increase the current applied to laser diode 702 for a first period of time so that the current applied to laser diode 702 will provide a threshold charge to start emission of a light pulse. Subsequently, control circuit 700 may be configured to apply a voltage having an opposite polarity to laser diode 702 to reduce the current applied to laser diode 702 to discharge laser diode 702 and stop the emission of the light pulse.

For example, charging voltage source 704 may be configured to apply the voltage having the first polarity to laser diode 702. Switching circuit 708 may be configured to couple charging voltage source 704 to laser diode 702 during the first time period. Discharging voltage source 706 may be configured to apply the voltage having the opposite polarity to laser diode 702. Switching circuit 708 may be configured to couple discharging voltage source 706 to laser diode 702 during the second time period. Examples of switching circuit 708 are described herein.

Figure 8:
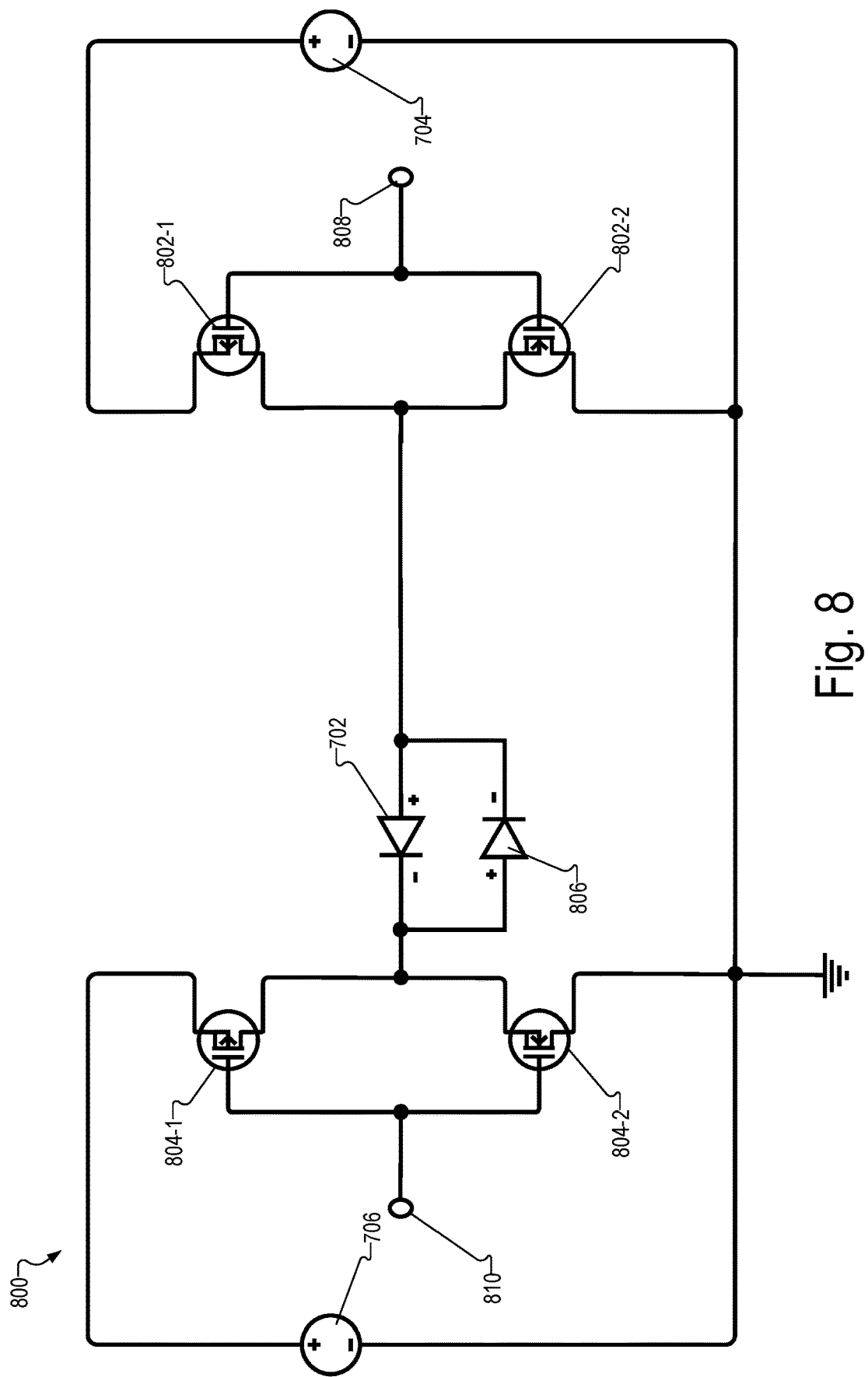

For instance, FIG. 8 shows an exemplary configuration 800 of control circuit 700. Configuration 800 includes laser diode 702, charging voltage source 704, and discharging voltage source 706. Configuration 800 further includes an implementation of switching circuit 708 that includes a first set of transistors 802 (e.g., transistor 802-1 and transistor 802-2) and a second set of transistors 804 (e.g., transistor 804-1 and transistor 804-2). Configuration 800 further includes a reverse diode 806. Reverse diode 806 may be coupled antiparallel to laser diode 702 to protect laser diode 702 against a reverse voltage applied accidentally or induced by stray inductances in control circuit 700. In some alternative implementations, control circuit 700 does not include reverse diode 806.

Transistors 802 are controlled by a control signal 808, while transistors 804 are controlled by a control signal 810. Transistors 802 may be configured such that control signal 808 may turn off one of transistors 802 while turning on the other of transistors 802 and vice versa. Transistors 804 may be configured to be similarly controlled by control signal 810. For example, in configuration 800, transistor 802-1 and transistor 804-1 are P-channel metal-oxide-semiconductor field-effect transistors (MOSFETs). Transistor 802-2 and transistor 804-2 are N-channel MOSFETs. Thus, a high signal provided as control signal 808 may turn off transistor 802-1 and turn on transistor 802-2, while a low signal provided as control signal 808 may turn on transistor 802-1 and turn off transistor 802-2. Similarly, a high signal provided as control signal 810 may turn off transistor 804-1 and turn on transistor 804-2, while a low signal provided as control signal 810 may turn on transistor 804-1 and turn off transistor 804-2. Based on timings of control signal 808 and control signal 810, voltages of opposite polarities may be applied to laser diode 702 to control a current applied to laser diode 702 and consequently, a light pulse emitted by laser diode 702.

Figure 9:
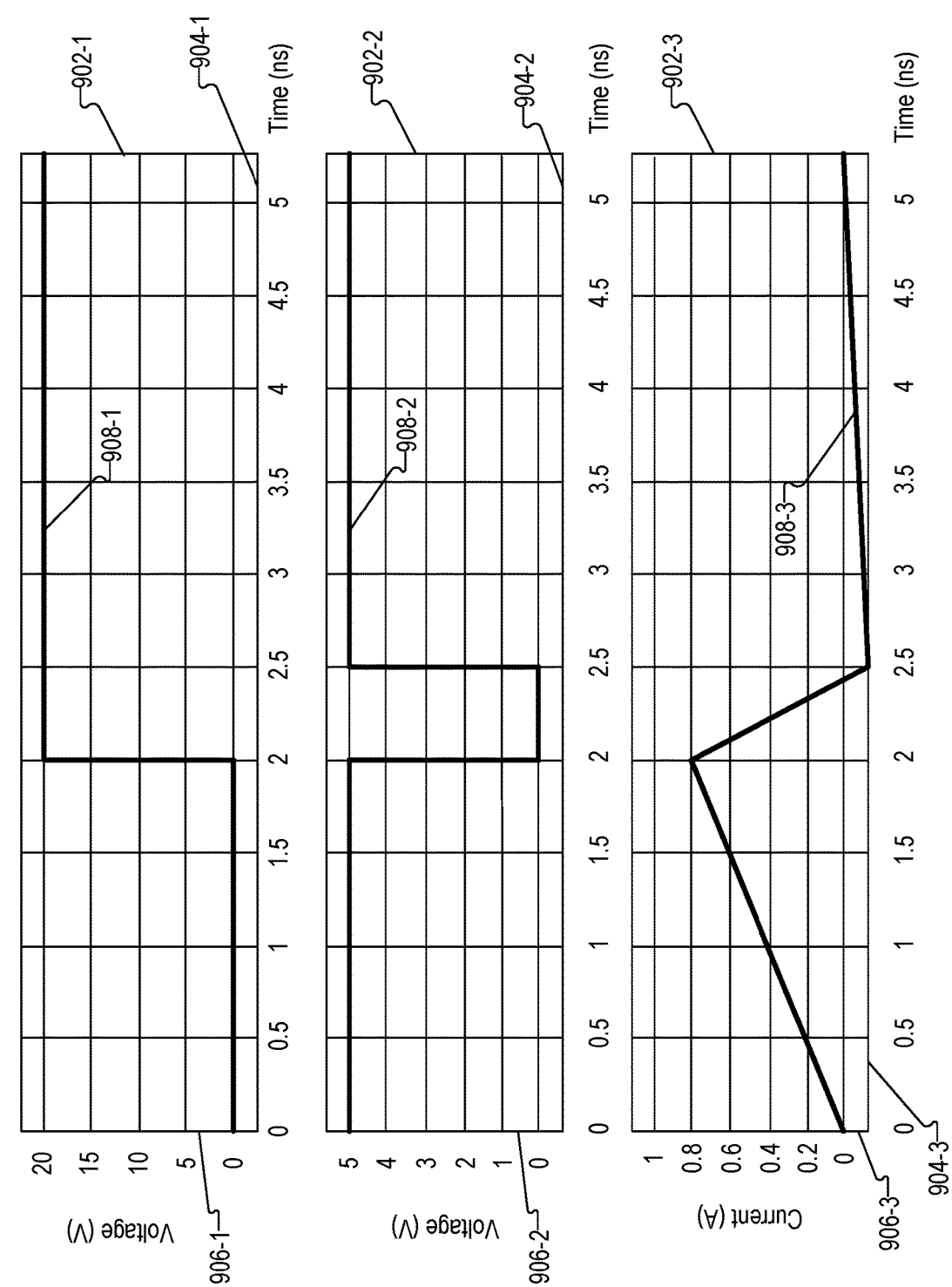
FIG. 9 shows an exemplary timing diagram for the control circuit.

FIG. 9 shows an exemplary timing diagram 900 for a control circuit such as configuration 800. Timing diagram 900 includes a graph 902-1 showing timing of control signal 808, a graph 902-2 showing timing of control signal 810, and a graph 902-3 showing timing of a resulting current applied to laser diode 702.

Graph 902-1 includes an x-axis 904-1 representing time (in nanoseconds (ns)) and a y-axis 906-1 representing voltage (in volts (V)) provided as control signal 808. Graph 902-1 further includes a line 908-1 that shows control signal 808 output over time. Similarly, graph 902-2 includes an x-axis 904-2 representing a same timeline as x-axis 904-1 of graph 902-1 and a y-axis 906-2 representing voltage (V) provided as control signal 810. Graph 902-2 further includes a line 908-2 that shows control signal 810 over time. Graph 902-3 includes an x-axis 904-3 representing the same timeline as x-axis 904-1 and a y-axis 906-3 representing a current (in amperes (A)) applied to laser diode 702. Graph 902-3 further includes a line 908-3 that shows the current over time.

In this example, for a first time period from time 0 ns to 2 ns, line 908-1 shows the voltage of control signal 808 is 0 V, thus providing a low signal to transistors 802. As a result, transistor 802-1 is on and transistor 802-2 is off. During the same first time period, line 908-2 shows the voltage of control signal 810 is at 20 V, which may be a voltage level provided by discharging voltage source 706. Thus, control signal 810 provides a high signal to transistors 804, turning off transistor 804-1 and turning on transistor 804-2. Consequently, charging voltage source 704 is coupled to laser diode 702 through transistor 802-1 and then to ground through transistor 804-2, allowing the current applied to laser diode 702 to increase, as shown by line 908-3, from 0 A to 0.8 A. Stray inductances in control circuit 700 may affect a slew rate of the current increase, and as a result, a duration of the first time period.

By 2 ns, laser diode 702 may be sufficiently charged to begin emitting a light pulse. At this time, the current applied to laser diode 702 may be reduced so that the emission of the light pulse is stopped to provide a light pulse with a short duration without oscillation. As shown, from 2 ns to 2.5 ns may be a second time period during which line 908-1 shows the voltage of control signal 808 is set to 5 V, which may be a voltage level provided by charging voltage source 704. Thus, control signal 808 provides a high signal to transistors 802, turning off transistor 802-1 and turning on transistor 802-2. Meanwhile, line 908-2 shows the voltage of control signal 810 is set to 0 V, providing a low signal to transistors 804. As a result, transistor 804-1 turns on and transistor 804-2 turns off. Consequently, discharging voltage source 706 is coupled to laser diode 702 through transistor 804-1 and then to ground through transistor 802-2, which reverses a polarity of the voltage applied to laser diode 702. As a result, the current applied to laser diode 702 drops, as shown by line 908-3, from 0.8 A to −0.2 A. Such a drop in the current applied to laser diode 702 may rapidly discharge laser diode 702 to stop the emission of the light pulse.

Once the light pulse emission is stopped at 2.5 ns, control signal 808 may remain high while control signal 810 is also set to high, as shown by lines 908-1 and 908-2, respectively. Having both control signals 808 and 810 set to high results in transistors 802-1 and 804-1 turning off and transistors 802-2 and 804-2 turning on. Thus, laser diode 702 is disconnected from both charging voltage source 704 and discharging voltage source 706 and the current applied to laser diode 702 decays to 0 A, as shown by line 908-3.

In this manner, control circuit 700 may drive laser diode 702 to emit a light pulse of any suitable duration. For instance, a charging slew rate of the increasing current applied to laser diode 702 during the first time period may be controlled based on a voltage level output by charging voltage source 704. By increasing the output voltage from 5 V to a higher voltage level, the charging slew rate may be increased so that the first time period during which the current applied to laser diode 702 increases is shortened. Conversely, decreasing the output voltage may decrease the charging slew rate and lengthen the first time period. Likewise, a discharging slew rate of the decreasing current applied to laser diode 702 during the second time period may be controlled based on a voltage level output by discharging voltage source 706. The output voltage levels for either or both of charging voltage source 704 and discharging voltage source 706 may be calibrated based on a current profile or any other suitable characteristic of laser diode 702 and/or driving conditions (e.g., temperature or any other suitable condition) of laser diode 702. Such calibration may result in a reduction of power dissipation of an overall circuit including control circuit 700 and laser diode 702. Additionally or alternatively, charging voltage source 704 and/or discharging voltage source 706 may be adjustable voltage sources that are included in a closed-loop system. The closed-loop system may include one or more photodetectors (e.g., SPADs) that provide output regarding the light pulses generated by laser diode 702 as feedback to control circuit 700. Based on the feedback, charging voltage source 704 and/or discharging voltage source 706 may be adjusted to adjust the charging and/or discharging slew rates.

Figure 10:
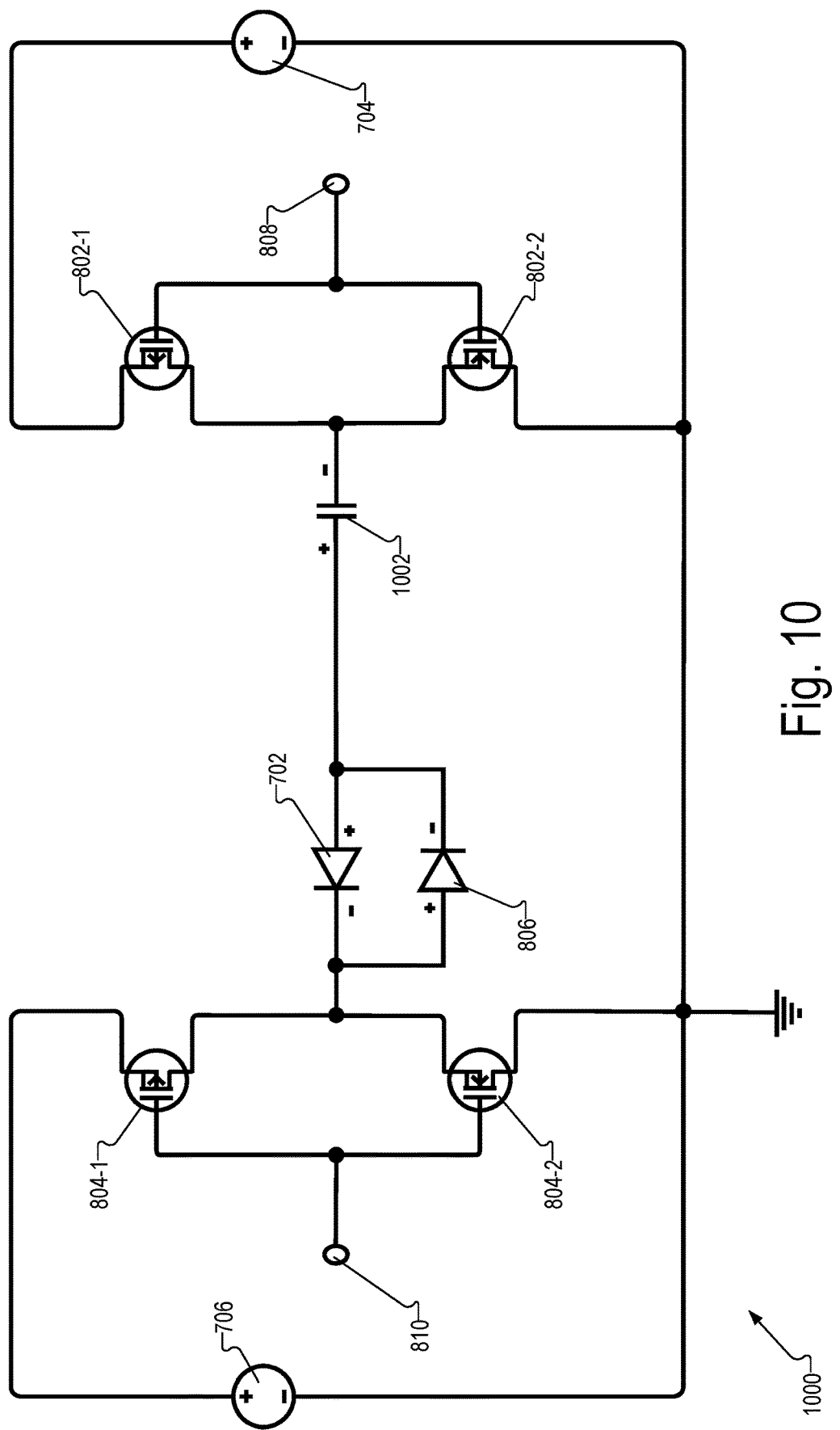
FIGS. 10-11 show exemplary control circuits for a laser diode.

FIG. 10 shows another exemplary configuration 1000 of control circuit 700. Configuration 1000 includes laser diode 702, charging voltage source 704, and discharging voltage source 706. Configuration 1000 also includes transistors 802 controlled by control signal 808, transistors 804 controlled by control signal 810, and reverse diode 806. Configuration further includes a capacitor 1002, which may be configured to provide direct current (DC) decoupling and provide a safety barrier in case one or more of transistors 802 and transistors 804 may fail. Capacitor 1002 may also be configured to provide a charge to laser diode 702, which may allow for a margin of error in timing accuracy of control signal 808 and/or control signal 810.

For example, capacitor 1002 may be charged through reverse diode 806 from discharging voltage source 706 by turning on transistor 804-1 and transistor 802-2 and turning off transistor 802-1 and transistor 804-2. Subsequently, transistor 804-2 may be turned on and transistor 804-1 may be turned off. As a result, capacitor 1002 may discharge to laser diode 702. Additionally, transistor 802-1 may be turned on and transistor 802-2 turned off so that charging voltage source 704 may also be coupled to laser diode 702 to apply additional voltage.

Figure 11:
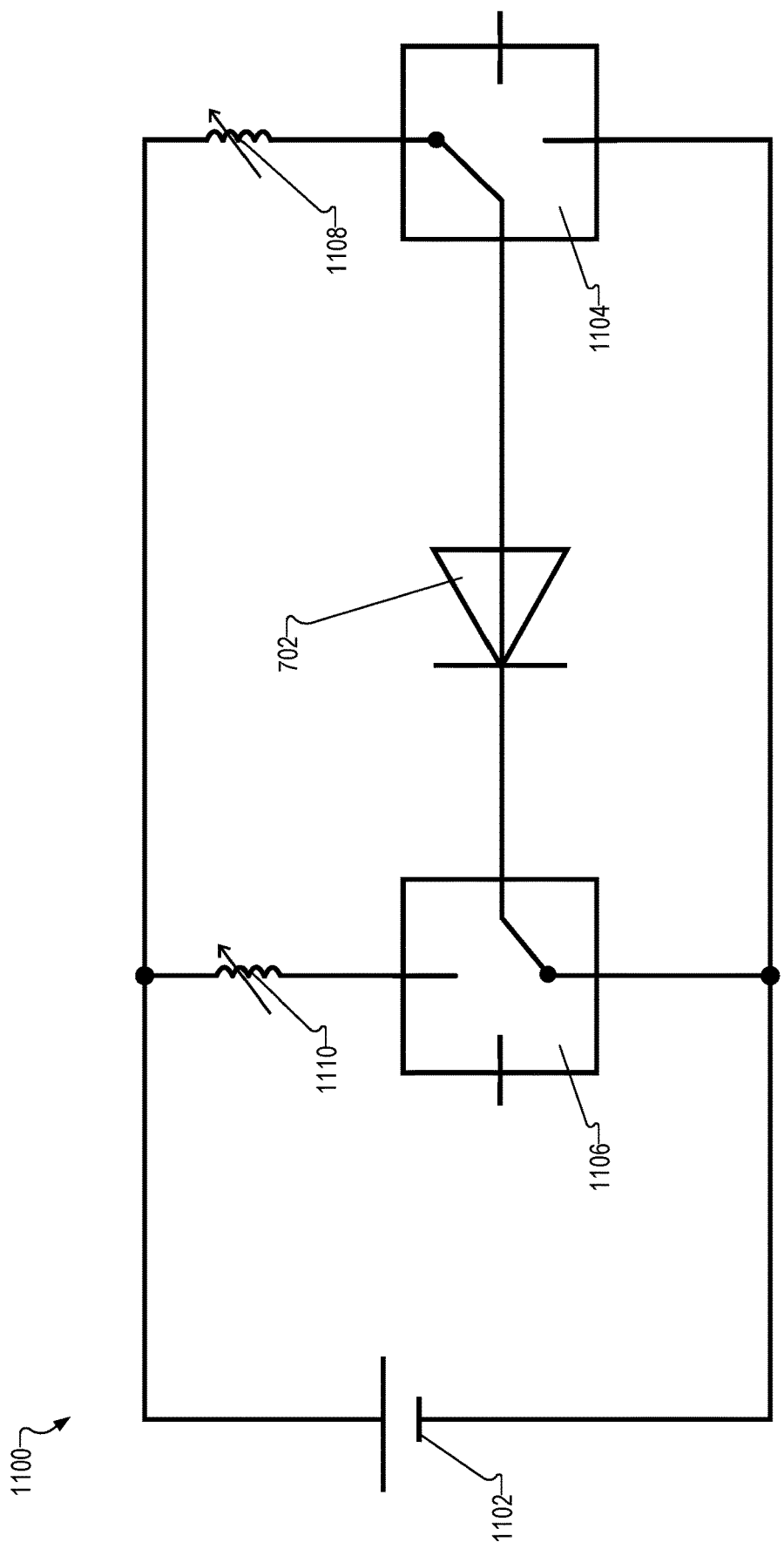

FIG. 11 shows another exemplary control circuit 1100 coupled to laser diode 702. Control circuit 1100 may be configured to control laser diode 702 in a manner similar to control circuit 700, reversing a polarity of a voltage applied to laser diode 702 to control slew rates of a current applied to laser diode 702. In contrast to control circuit 700, however, control circuit 1100 includes one voltage source 1102. Voltage source 1102 is selectively coupled to laser diode 702 via switching circuits 1104 and 1106. Control circuit 1100 further includes inductors 1108 and 1110.

Switching circuits 1104 and 1106 may be implemented by any suitable component or components configured to allow laser diode 702 to selectively couple to a cathode of voltage source 1102, an anode of voltage source 1102, or neither. Switching circuits 1104 and 1106 may be controlled in a manner similar to control circuit 700 (e.g., as described with configuration 800) to apply voltage having a first polarity to laser diode 702 to provide a threshold charge for laser diode 702 to start an emission of a light pulse and then apply voltage having a second polarity opposite the first polarity to laser diode 702 to discharge laser diode 702 to stop the emission of the light pulse. For example, switching circuit 1104 may couple the cathode of voltage source 1102 to laser diode 702 while switching circuit 1106 couples the anode of voltage source 1102 to laser diode 702. Thus, voltage having the first polarity is applied to laser diode 702 to provide the threshold charge for laser diode 702. Subsequently, switching circuit 1104 may couple the anode of voltage source 1102 to laser diode 702 while switching circuit 1106 couples the cathode of voltage source 1102 to laser diode 702 to apply voltage having the second polarity to laser diode 702 to discharge laser diode 702. Once laser diode 702 is discharged, switching circuits 1104 and 1106 may couple laser diode 702 to neither the cathode nor the anode of voltage source 1102, allowing current applied to laser diode 702 to decay to zero.

Inductor 1108 may be configured to control a charging slew rate of the current applied to laser diode 702 as the current increases to start the emission of the light pulse. Similarly, inductor 1110 may be configured to control a discharging slew rate of the current applied to laser diode 702 as the current decreases to stop the emission of the light pulse. In alternative examples, inductor 1108 and/or inductor 1110 may be not included. Additionally, a similar inductor or inductors may be included in configuration 800 or configuration 1000 to further control the charging slew rate or the discharging slew rate.

As mentioned, optical measurement system 100 may be at least partially wearable by a user. For example, optical measurement system 100 may be implemented by a wearable device configured to be worn by a user (e.g., a head-mountable component configured to be worn on a head of the user). The wearable device may include one or more photodetectors and/or any of the other components described herein. In some examples, one or more components (e.g., processor 108, controller 112, etc.) may not be included in the wearable device and/or included in a separate wearable device than the wearable device in which the one or more photodetectors are included. In these examples, one or more communication interfaces (e.g., cables, wireless interfaces, etc.) may be used to facilitate communication between the various components.

FIGS. 12-17 illustrate embodiments of a wearable device 1200 that includes elements of the optical detection systems described herein. In particular, the wearable devices 1200 include a plurality of modules 1202, similar to the modules shown in FIG. 6 as described herein. For example, each module 1202 includes a source 604 and a plurality of detectors 606 (e.g., detectors 606-1 through 606-6). Source 604 may be implemented by one or more light sources similar to light source 110. Each detector 606 may implement or be similar to detector 104 and may include a plurality of photodetectors. The wearable devices 1200 may each also include a controller (e.g., controller 112) and a processor (e.g., processor 108) and/or be communicatively connected to a controller and processor. In general, wearable device 1200 may be implemented by any suitable headgear and/or clothing article configured to be worn by a user. The headgear and/or clothing article may include batteries, cables, and/or other peripherals for the components of the optical measurement systems described herein.

Figure 12:
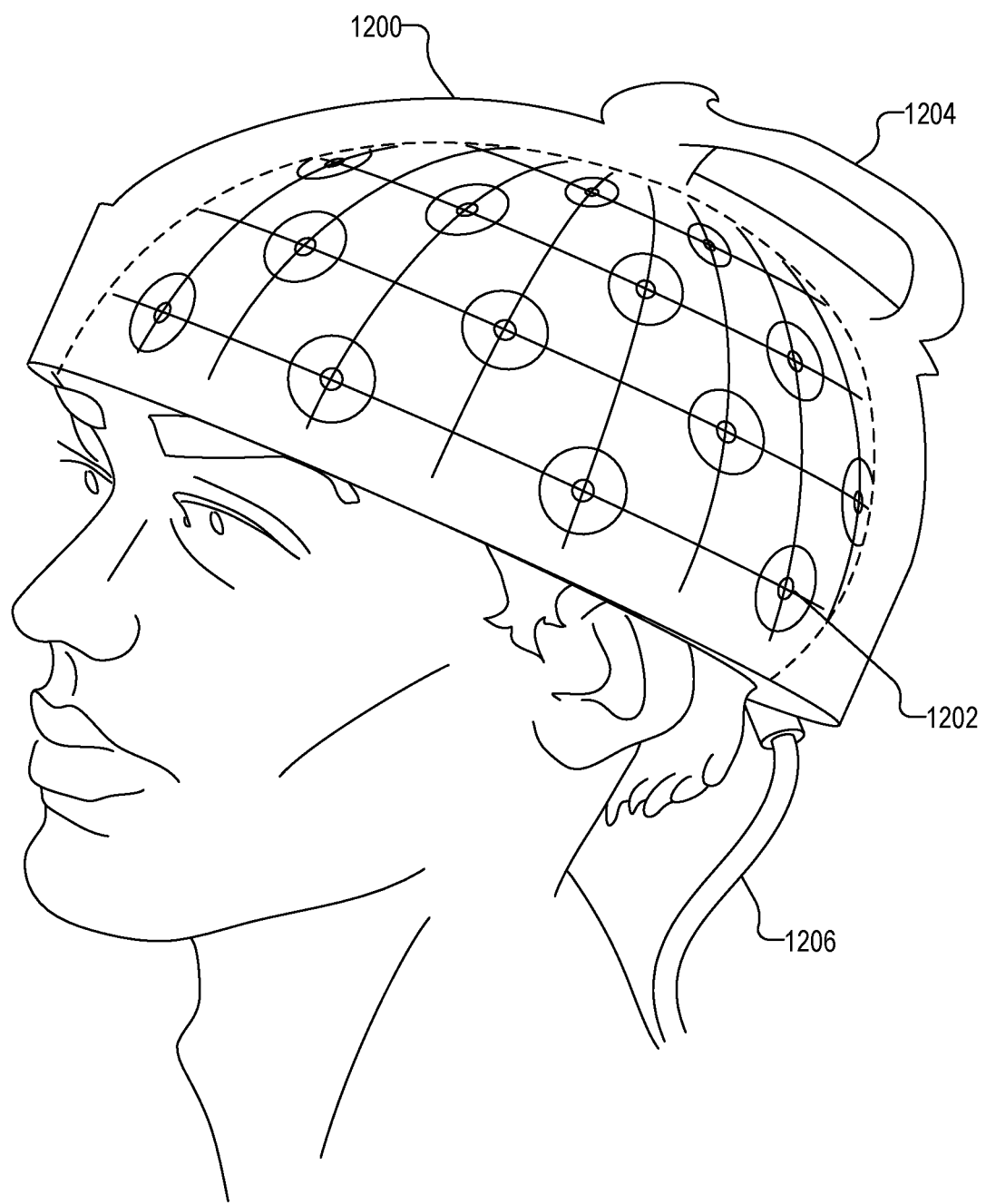
FIGS. 12-17 illustrate embodiments of a wearable device that includes elements of the optical measurement systems described herein.
Figure 13:
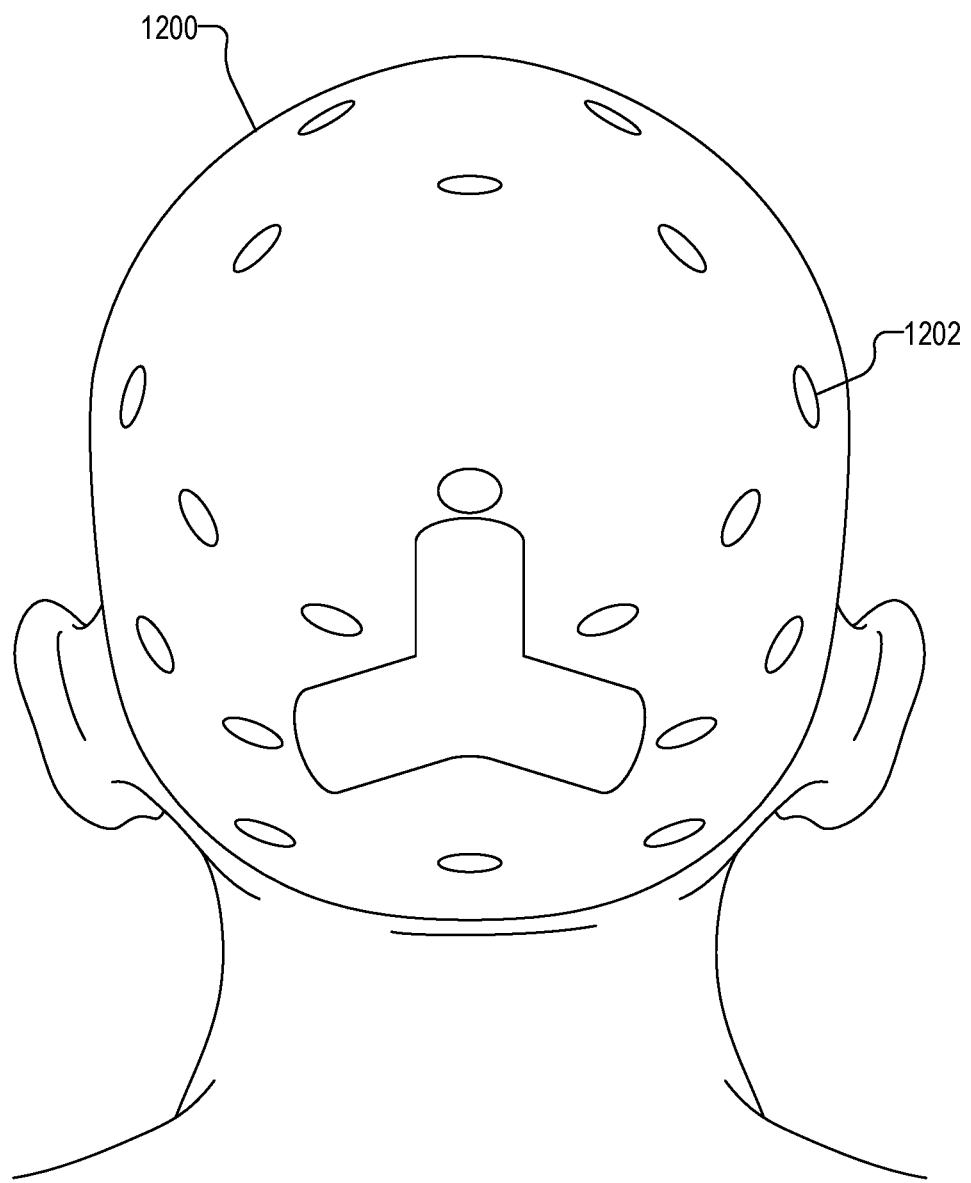
Figure 14:
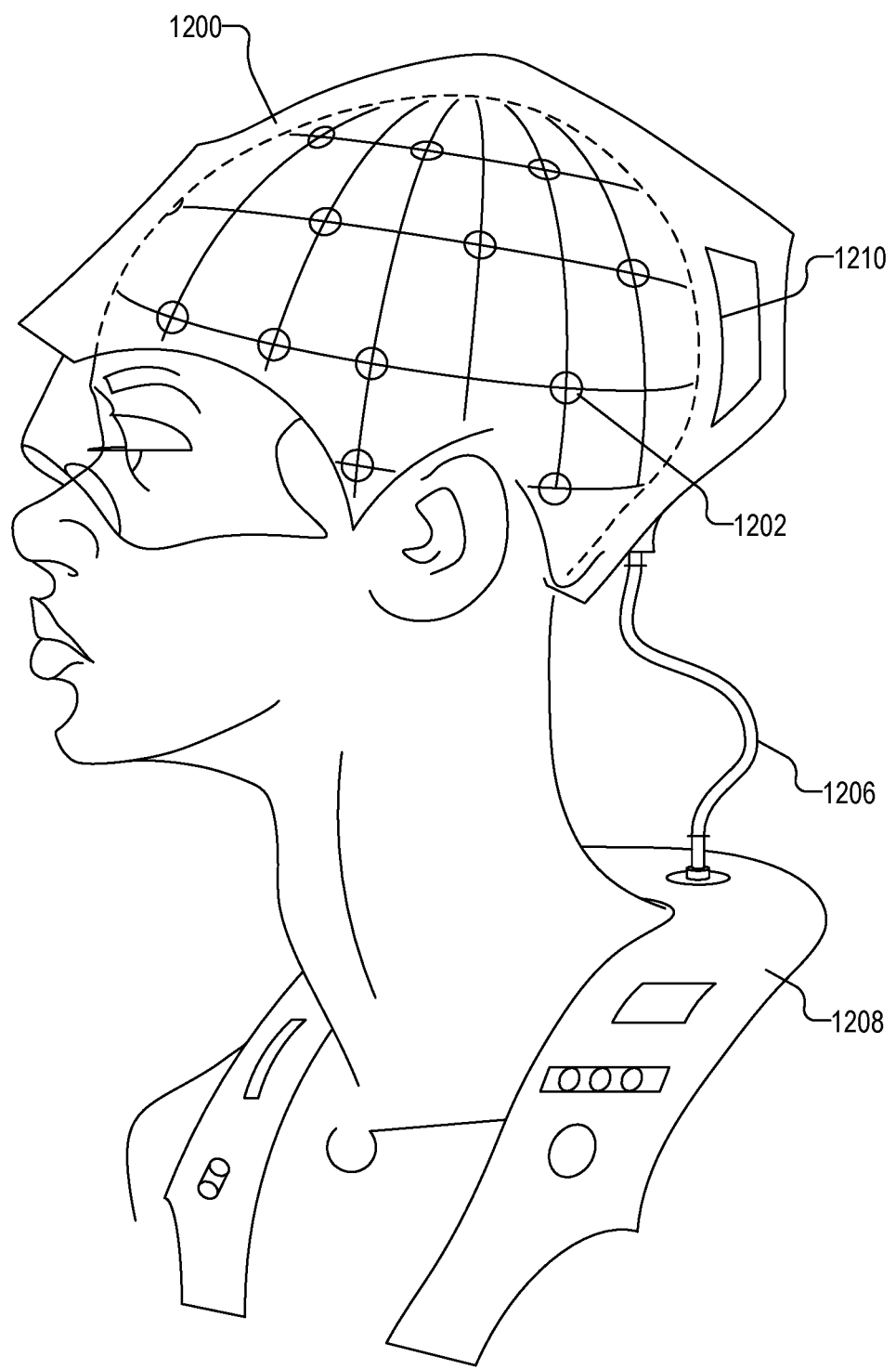

FIG. 12 illustrates an embodiment of a wearable device 1200 in the form of a helmet with a handle 1204. A cable 1206 extends from the wearable device 1200 for attachment to a battery or hub (with components such as a processor or the like). FIG. 13 illustrates another embodiment of a wearable device 1200 in the form of a helmet showing a back view. FIG. 14 illustrates a third embodiment of a wearable device 1200 in the form of a helmet with the cable 1206 leading to a wearable garment 1208 (such as a vest or partial vest) that can include a battery or a hub. Alternatively or additionally, the wearable device 1200 can include a crest 1210 or other protrusion for placement of the hub or battery.

Figure 15:
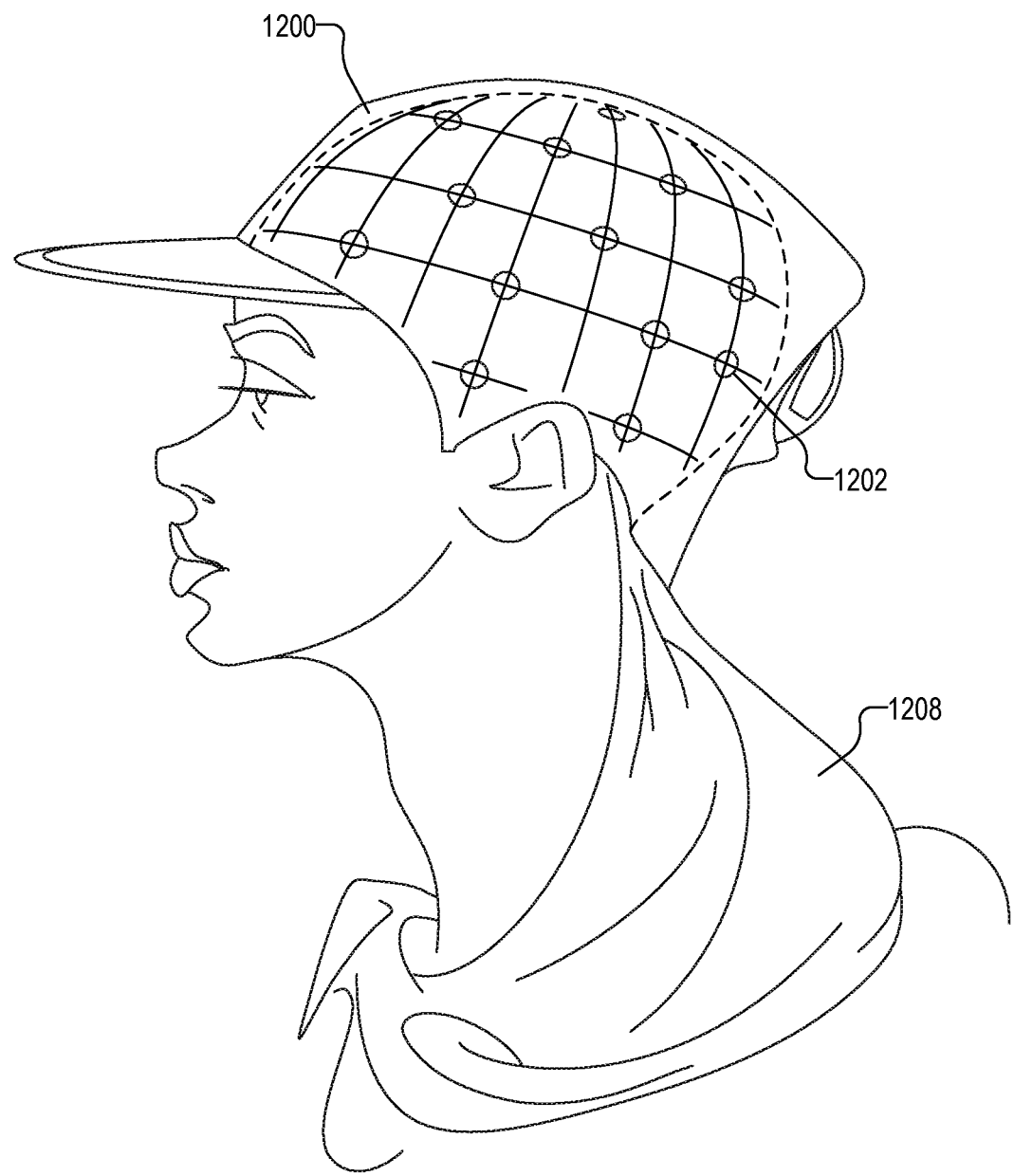
Figure 16:
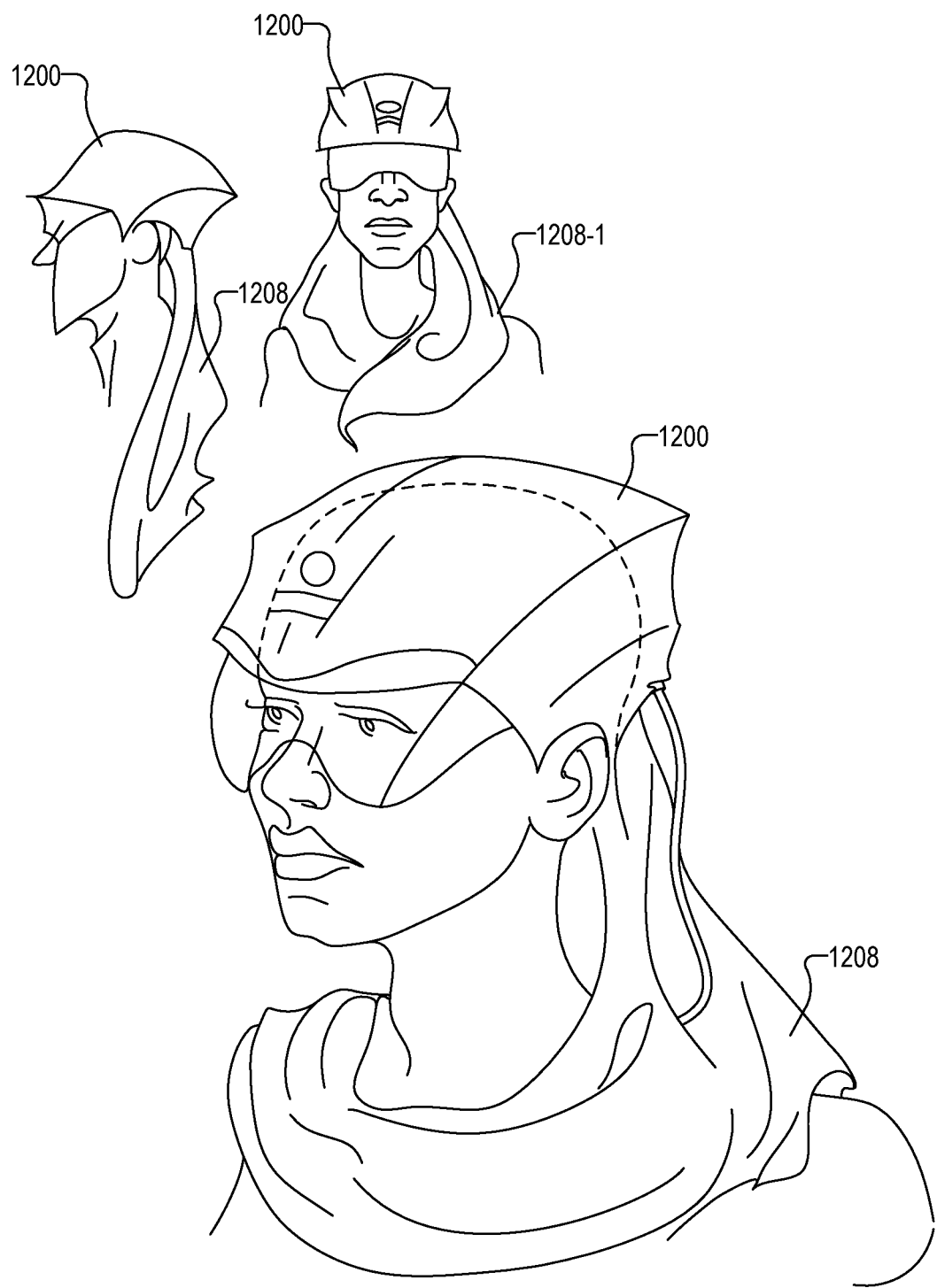
Figure 17:
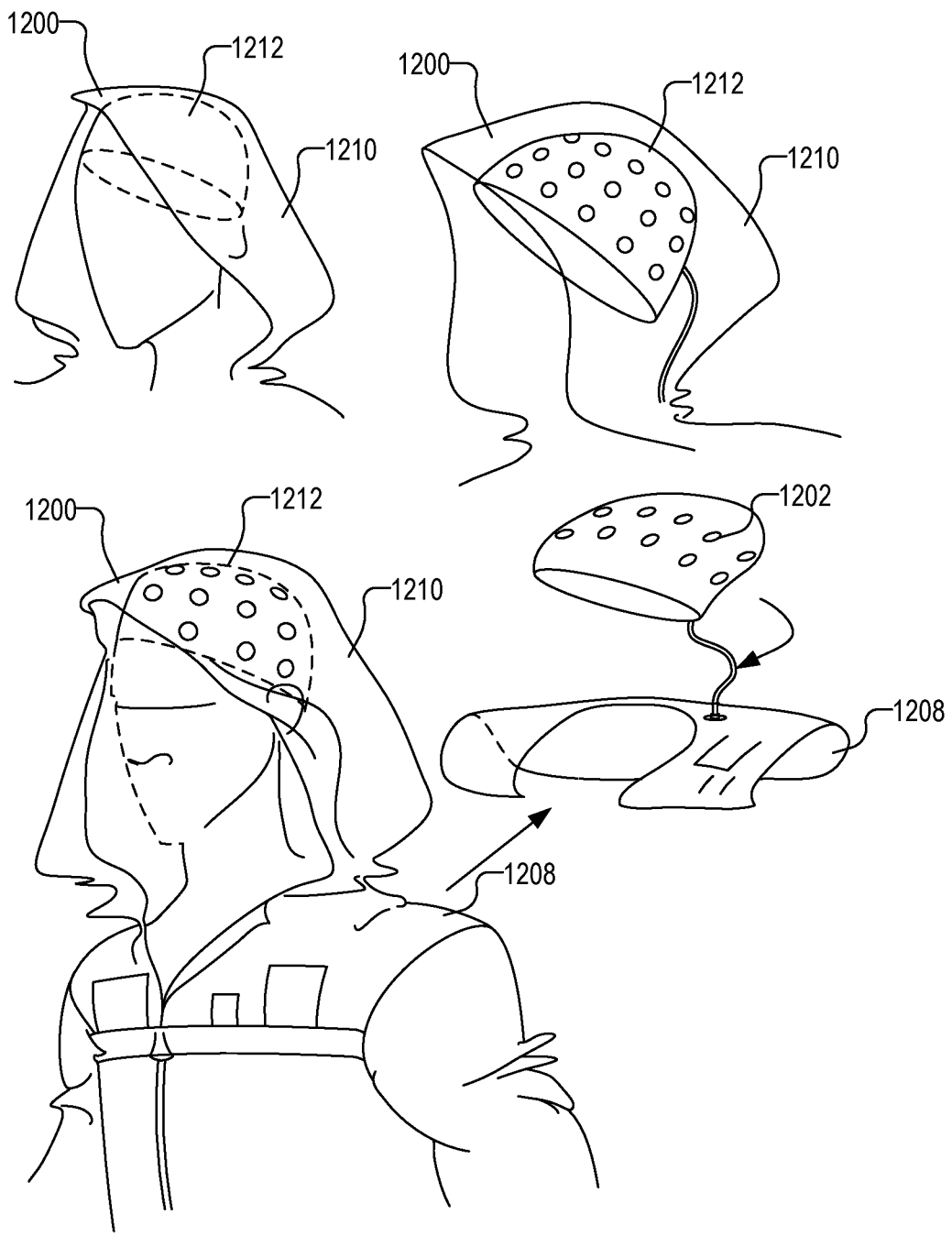

FIG. 15 illustrates another embodiment of a wearable device 1200 in the form of a cap with a wearable garment 1208 in the form of a scarf that may contain or conceal a cable, battery, and/or hub. FIG. 16 illustrates additional embodiments of a wearable device 1200 in the form of a helmet with a one-piece scarf 1208 or two-piece scarf 1208-1. FIG. 17 illustrates an embodiment of a wearable device 1200 that includes a hood 1210 and a beanie 1212 which contains the modules 1202, as well as a wearable garment 1208 that may contain a battery or hub.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 18:
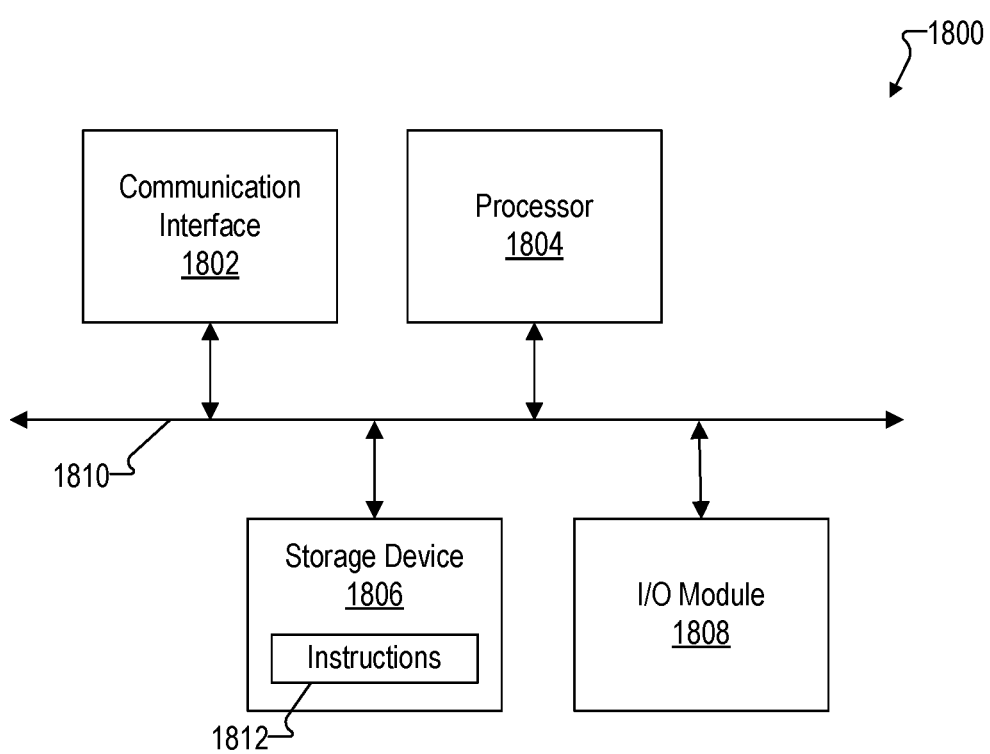
FIG. 18 illustrates an exemplary computing device.

FIG. 18 illustrates an exemplary computing device 1800 that may be specifically configured to perform one or more of the processes described herein. Any of the systems, units, computing devices, and/or other components described herein may be implemented by computing device 1800.

As shown in FIG. 18, computing device 1800 may include a communication interface 1802, a processor 1804, a storage device 1806, and an input/output ("I/O") module 1808 communicatively connected one to another via a communication infrastructure 1810. While an exemplary computing device 1800 is shown in FIG. 18, the components illustrated in FIG. 18 are not intended to be limiting. Additional or alternative components may be used in other embodiments. Components of computing device 1800 shown in FIG. 18 will now be described in additional detail.

Communication interface 1802 may be configured to communicate with one or more computing devices. Examples of communication interface 1802 include, without limitation, a wired network interface (such as a network interface card), a wireless network interface (such as a wireless network interface card), a modem, an audio/video connection, and any other suitable interface.

Processor 1804 generally represents any type or form of processing unit capable of processing data and/or interpreting, executing, and/or directing execution of one or more of the instructions, processes, and/or operations described herein. Processor 1804 may perform operations by executing computer-executable instructions 1812 (e.g., an application, software, code, and/or other executable data instance) stored in storage device 1806.

Storage device 1806 may include one or more data storage media, devices, or configurations and may employ any type, form, and combination of data storage media and/or device. For example, storage device 1806 may include, but is not limited to, any combination of the non-volatile media and/or volatile media described herein. Electronic data, including data described herein, may be temporarily and/or permanently stored in storage device 1806. For example, data representative of computer-executable instructions 1812 configured to direct processor 1804 to perform any of the operations described herein may be stored within storage device 1806. In some examples, data may be arranged in one or more databases residing within storage device 1806.

I/O module 1808 may include one or more I/O modules configured to receive user input and provide user output. I/O module 1808 may include any hardware, firmware, software, or combination thereof supportive of input and output capabilities. For example, I/O module 1808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1808 is configured to provide graphical data to a display for presentation to a user. The graphical data may be representative of one or more graphical user interfaces and/or any other graphical content as may serve a particular implementation.

Figure 19:
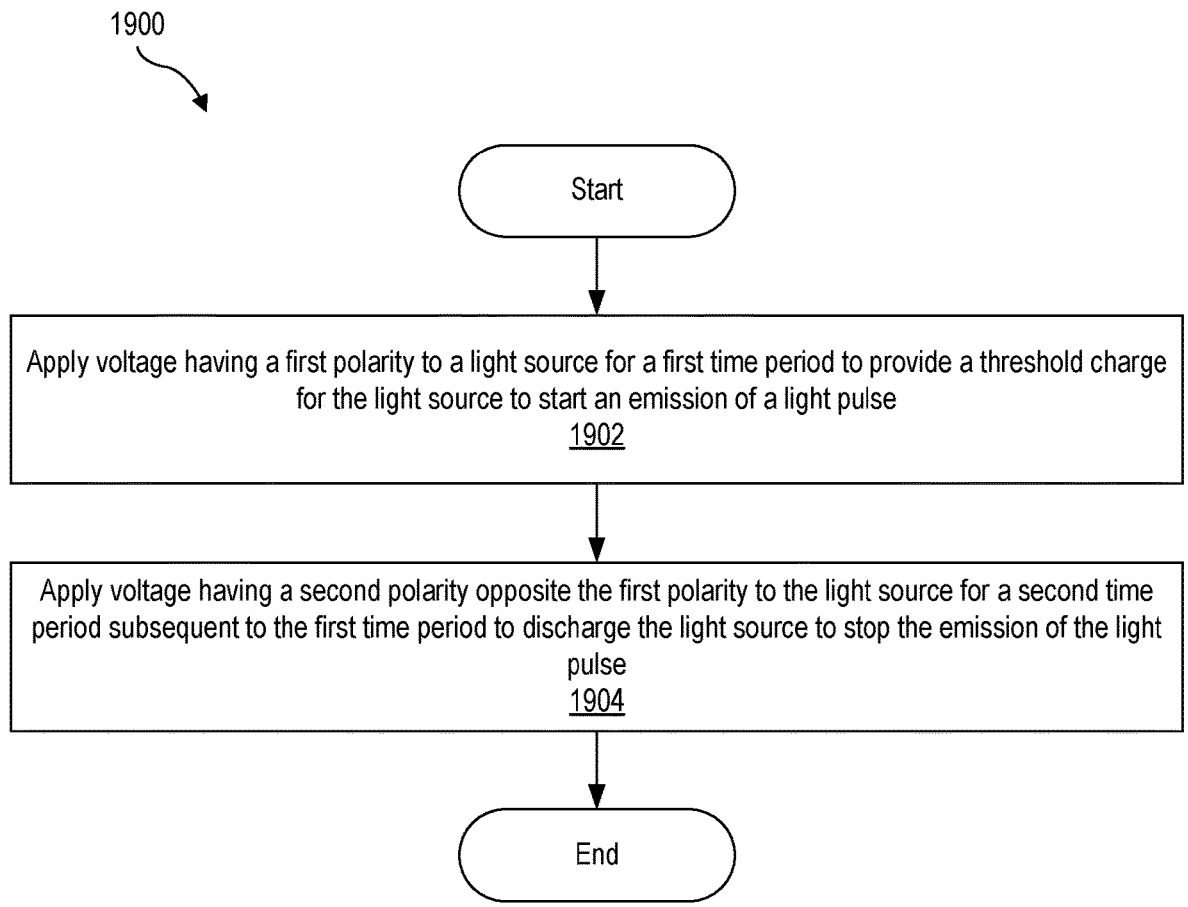
FIG. 19 illustrates an exemplary method.

FIG. 19 illustrates an exemplary method 1900 that may be performed by control circuit 700 and/or any implementation thereof. While FIG. 19 illustrates exemplary operations according to one embodiment, other embodiments may omit, add to, reorder, and/or modify any of the operations shown in FIG. 19.

In operation 1902, a control circuit applies voltage having a first polarity to a light source for a first time period to provide a threshold charge for the light source to start an emission of a light pulse. Operation 1902 may be performed in any of the ways described herein.

In operation 1904, the control circuit applies voltage having a second polarity opposite the first polarity to the light source for a second time period subsequent to the first time period to discharge the light source to stop the emission of the light pulse. Operation 1904 may be performed in any of the ways described herein.

An exemplary optical measurement system described herein includes a light source and a control circuit. The control circuit is configured to apply voltage having a first polarity to the light source for a first time period to provide a threshold charge for the light source to start an emission of a light pulse that is directed at a target within a body. The control circuit is further configured to apply voltage having a second polarity opposite the first polarity to the light source for a second time period subsequent to the first time period to discharge the light source to stop the emission of the light pulse.

An exemplary system described herein includes a single photon avalanche diode (SPAD) configured to detect a photon from a light pulse after the light pulse reflects off a target within a body, a fast gating circuit configured to arm and disarm the SPAD, a light source, and a control circuit. The control circuit is configured to apply voltage having a first polarity to the light source for a first time period to provide a threshold charge for the light source to start an emission of the light pulse. The control circuit is further configured to apply voltage having a second polarity opposite the first polarity to the light source for a second time period subsequent to the first time period to discharge the light source to stop the emission of the light pulse.

An exemplary wearable system for use by a user described herein includes a head-mountable component configured to be attached to a head of the user, a light source, and a control circuit. The head-mountable component includes a photodetector configured to detect a photon from a light pulse after the light pulse reflects off a target within the head. The control circuit is configured to apply voltage having a first polarity to the light source for a first time period to provide a threshold charge for the light source to start an emission of a light pulse. The control circuit is further configured to apply voltage having a second polarity opposite the first polarity to the light source for a second time period subsequent to the first time period to discharge the light source to stop the emission of the light pulse.

An exemplary method described herein includes applying, by a control circuit, voltage having a first polarity to a light source for a first time period to provide a threshold charge for the light source to start an emission of a light pulse. The method further includes applying, by the control circuit, voltage having a second polarity opposite the first polarity to the light source for a second time period subsequent to the first time period to discharge the light source to stop the emission of the light pulse.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. An optical measurement system comprising:
   a light source; and
   a control circuit configured to:
      apply voltage having a first polarity to the light source for a first time period to provide a threshold charge for the light source to start an emission of a light pulse, and
      apply voltage having a second polarity opposite the first polarity to the light source for a second time period subsequent to the first time period to discharge the light source to stop the emission of the light pulse.

2. The optical measurement system of claim 1, wherein the second time period is at least of a duration such that a negative current is applied to the light source.

3. The optical measurement system of claim 1, wherein the control circuit comprises:
   a first voltage source configured to apply the voltage having the first polarity;
   a second voltage source configured to apply the voltage having the second polarity; and
   a switching circuit configured to selectively couple the first voltage source to the light source and the second voltage source to the light source.

4. The optical measurement system of claim 3, wherein:
   the switching circuit includes:
      a first transistor and a second transistor coupled to the first voltage source and the light source, and
      a third transistor and a fourth transistor coupled to the second voltage source and the light source;
   the first transistor and the fourth transistor are on and the second transistor and the third are off during the first time period; and
   the second transistor and the third transistor are on and the first transistor and the fourth transistor are off during the second time period.

5. The optical measurement system of claim 3, wherein:
   the first voltage source is adjustable to control a charging slew rate of a current applied to the light source that increases to start the emission of the light pulse; and
   and the second voltage source is adjustable to control a discharging slew rate of the current applied to the light source that decreases to stop the emission of the light pulse.

6. The optical measurement system of claim 1, wherein the control circuit comprises an inductor coupled to the light source to control a slew rate of at least one of:
   increasing a current applied to the light source; and
   decreasing the current applied to the light source.

7. The optical measurement system of claim 1, wherein at least one of a duration of the first time period and a duration of the second time period are configured based on a characteristic of the light source.

8. The optical measurement system of claim 1, wherein the control circuit comprises:
   a voltage source;
   a first inductor coupled to the voltage source;
   a first switching circuit coupled to the first inductor and the light source;
   a second inductor coupled to the voltage source; and
   a second switching circuit coupled to the second inductor and the light source, wherein:
      the first switching circuit and the second switching circuit are configured to selectively couple the voltage source to the light source through the first inductor or the second inductor,
      the first inductor is configured to control a charging slew rate of a current applied to the light source that increases to start the emission of the light pulse, and
      the second inductor is configured to control a discharging slew rate of the current applied to the light source that decreases to stop the emission of the light pulse.

9. The optical measurement system of claim 1, further comprising a photodetector configured to detect a photon from the light pulse after the light pulse reflects off a target within a body.

10. The optical measurement system of claim 9, wherein the control circuit further comprises:
    a first adjustable voltage source configured to apply the voltage having the first polarity and configured to control a charging slew rate of a current applied to the light source that increases to start the emission of the light pulse;
    a second adjustable voltage source configured to apply the voltage having the second polarity and configured to control a discharging slew rate of the current applied to the light source that decreases to stop the emission of the light pulse; and
    wherein at least one of the charging slew rate and the discharging slew rate is specified based on an output of the photodetector.

11. The optical measurement system of claim 9, further comprising:
    an array of photodetectors including the photodetector; and
    a signal processing circuit that generates a histogram based on times that the array of photodetectors detect photons from the light pulse after the light pulse reflects off the target.

12. The optical measurement system of claim 9, wherein the photodetector comprises:
    a single photon avalanche diode (SPAD); and
    a fast gating circuit configured to arm and disarm the SPAD.

13. The optical measurement system of claim 9, wherein the photodetector is included in a wearable device configured to be worn by a user.

14. The optical measurement system of claim 13, wherein the wearable device includes a head-mountable component configured to be worn on a head of the user.

15. The optical measurement system of claim 1, wherein the light source includes a laser diode.

16. A system comprising:
    a single photon avalanche diode (SPAD) configured to detect a photon from a light pulse after the light pulse reflects off a target within a body;
    a fast gating circuit configured to arm and disarm the SPAD;
    a light source; and
    a control circuit configured to:

apply voltage having a first polarity to the light source for a first time period to provide a threshold charge for the light source to start an emission of the light pulse, and apply voltage having a second polarity opposite the first polarity to the light source for a second time period subsequent to the first time period to discharge the light source to stop the emission of the light pulse.

17. The system of claim 16, wherein the second time period is at least of a duration such that a negative current is applied to the light source.

18. The system of claim 16, wherein the control circuit comprises:
a first voltage source configured to apply the voltage having the first polarity;
a second voltage source configured to apply the voltage having the second polarity; and
a switching circuit configured to selectively couple the first voltage source to the light source and the second voltage source to the light source.

19. The system of claim 18, wherein:
the switching circuit includes:
a first transistor and a second transistor coupled to the first voltage source and the light source, and
a third transistor and a fourth transistor coupled to the second voltage source and the light source;
the first transistor and the fourth transistor are on and the second transistor and the third are off during the first time period; and
the second transistor and the third transistor are on and the first transistor and the fourth transistor are off during the second time period.

20. The system of claim 18, wherein:
the first voltage source is adjustable to control a charging slew rate of a current applied to the light source that increases to start the emission of the light pulse; and
and the second voltage source is adjustable to control a discharging slew rate of the current applied to the light source that decreases to stop the emission of the light pulse.

21. The system of claim 16, wherein the control circuit comprises an inductor coupled to the light source to control a slew rate of at least one of:
increasing a current applied to the light source; and
decreasing the current applied to the light source.

22. The system of claim 16, wherein at least one of a duration of the first time period and a duration of the second time period are configured based on a characteristic of the light source.

23. The system of claim 16, wherein the control circuit comprises:
a voltage source;
a first inductor coupled to the voltage source;
a first switching circuit coupled to the first inductor and the light source;
a second inductor coupled to the voltage source; and
a second switching circuit coupled to the second inductor and the light source, wherein:
the first switching circuit and the second switching circuit are configured to selectively couple the voltage source to the light source through the first inductor or the second inductor,
the first inductor is configured to control a charging slew rate of a current applied to the light source that increases to start the emission of the light pulse, and
the second inductor is configured to control a discharging slew rate of the current applied to the light source that decreases to stop the emission of the light pulse.

24. The system of claim 16, wherein the control circuit further comprises:
a first adjustable voltage source configured to apply the voltage having the first polarity and configured to control a charging slew rate of a current applied to the light source that increases to start the emission of the light pulse;
a second adjustable voltage source configured to apply the voltage having the second polarity and configured to control a discharging slew rate of the current applied to the light source that decreases to stop the emission of the light pulse; and
wherein at least one of the charging slew rate and the discharging slew rate is specified based on an output of the SPAD.

25. The system of claim 16, further comprising:
an array of SPADs including the SPAD; and
a signal processing circuit that generates a histogram based on times that the array of SPADs detect photons from the light pulse after the light pulse reflects off the target.

26. The system of claim 16, wherein the SPAD is included in a wearable device configured to be worn by a user.

27. The system of claim 26, wherein the wearable device includes a head-mountable component configured to be worn on a head of the user.

28. The system of claim 16, wherein the light source includes a laser diode.

* * * * *